(12) United States Patent
Sugiyama et al.

(10) Patent No.: US 7,456,294 B2
(45) Date of Patent: Nov. 25, 2008

(54) HAIRPIN POLYAMIDE

(75) Inventors: Hiroshi Sugiyama, Tokyo (JP);
Toshikazu Bando, Tokyo (JP); Isao Saito, Kyoto (JP)

(73) Assignee: Japan Science and Technology Agency, Saitama (JP)

( * ) Notice: Subject to any disclaimer, the term of this patent is extended or adjusted under 35 U.S.C. 154(b) by 439 days.

(21) Appl. No.: 10/507,004

(22) PCT Filed: Mar. 3, 2003

(86) PCT No.: PCT/JP03/02423

§ 371 (c)(1),
(2), (4) Date: Sep. 8, 2004

(87) PCT Pub. No.: WO03/076412

PCT Pub. Date: Sep. 18, 2003

(65) Prior Publication Data

US 2005/0176647 A1 Aug. 11, 2005

(30) Foreign Application Priority Data

Mar. 8, 2002 (JP) .............................. 2002-063608

(51) Int. Cl.
*A61K 31/407* (2006.01)
*C07D 403/14* (2006.01)
(52) U.S. Cl. .................. 548/311.4; 548/311.7; 530/330
(58) Field of Classification Search ............... 548/311.4, 548/311.7
See application file for complete search history.

(56) References Cited

U.S. PATENT DOCUMENTS 5,843,937 A 12/1998 Wang et al.
6,143,901 A * 11/2000 Dervan ..................... 548/312.4

FOREIGN PATENT DOCUMENTS

| JP | 2000-511893 | | 9/2000 |
| JP | 2000-281679 | A | 10/2000 |
| WO | WO 97/44000 | | 11/1997 |
| WO | WO-00/15641 | A1 | 3/2000 |
| WO | WO-01/36677 | A1 | 5/2001 |
| WO | WO-01/85733 | A1 | 11/2001 |

OTHER PUBLICATIONS

Golub et al., Science, vol. 286, Oct. 15, 1999, pp. 531-537.*
Japanese Office Action for corresponding Japanese Patent Application No. 2002-063608, Aug. 2006.
International Search Report dated May 27, 2003, PCT/JP03/02423.
Dervan, Peter B., "Molecular Recognition of DNA by Small Molecules," Bioorganic & Medicinal Chemistry, vol. 9, pp. 2215-2235, Pergamon, Elsevier Science Ltd. (2001).
Wemmer et al., "Targeting the Minor Groove of DNA," Nucleic Acids, Current Opinion in Structural Biology, vol. 7, pp. 355-361, Current Biology Ltd. (1997).
Turner et al., "Recognition of Seven Base Pair Sequences in the Minor Groove of DNA by Ten-Ring Pyrrole-Imidazole Polyamide Hairpins," J. Am. Chem. Soc., vol. 119, pp. 7636-7644, American Chemical Society (1997).
Trauger et al., "Recoginition of 16 Base Pairs in the Minor Groove of DNA by a Pyrrole-Imidazole Polyamide Dimer," J. Am. Chem. Soc., vol. 120, pp. 3534-3535, American Chemical Society (1998).
Turner et al., "Aliphatic/Aromatic Amino Acid Pairings for Polyamide Recognition in the Minor Groove of DNA," J. Am. Chem. Soc., vol. 120, pp. 6219-6226, American Chemical Society (1998).
Gottesfeld et al., "Regulation of Gene Expression by Small Molecules," Letters to Nature, vol. 387, pp. 202-205 (May 8, 1997).
Dickinson, et al., "Inhibition of RNA Polymerase II Transcription in Human Cells by Synthetic DNA-binding ligands," Proc. Nat. Acad. of Sci. USA, Biochemistry, vol. 95, pp. 12890-12895, National Academy of Sciences, (Oct. 1998).
Chang et al., "Strand Selective Cleavage of DNA by Diastereomers of Hairpin Polyamide-seco-CBI Conjugates," J. Am. Chem. Soc., vol. 122. 4856-4864, American Chemical Society (2000).
Tao et al., "Rational Design of Sequence-Specific DNA Alkylating Agents Based on Duocarmycin A and Pyrrole-Imidazole Hairpin Polyamides," J. Am. Chem. Soc., vol. 121, pp. 4961-4967, American Chemcial Society (1999).
Sugiyama et al., "Covalent Alkylation of DNA with Duocarmycin A. Identification of Abasic Site Structure," Tetrahedron Letters, vol. 31, No. 49, pp. 7197-7200, Pergamon Press plc (1990).
Sugiyama et al., "A Novel Guanine N3 Alkylation by Antitumor Antibiotic Duocarmycin A," Tetrahedron Letter, vol. 34, No. 13, pp. 2179-2182, Pergamon Press Ltd. (1993).
Boger et al., "An Improved Synthesis of 1,2,9,9a-Tetrahydrocyclopropa[c]benz[e]indol-4-one (CBI): A Simplified Analogue of the CC-1065 Alkylation Subunit," J. Org. Chem., vol. 57, pp. 2873-2876, American Chemical Society (1992).
Boger et al., "An Efficient Synthesis of 1,2,9,9a-Tetrahydrocyclopropa[c]benz[e]indol-4-one (CBI): An Enhanced and Simplified Analog of the CC-1065 and Duocarmycin Alkylation Subunits," J. Org. Chem, vol. 60, pp. 1271-1275, American Chemical Society (1995).

(Continued)

Primary Examiner—Laura L Stockton
(74) Attorney, Agent, or Firm—Rader, Fishman & Grauer, PLLC

(57) ABSTRACT

It is intended to provide a pyrrole-imidazole polyamide type functional molecule having enhanced abilities of alkylating DNA and recognizing a sequence, compared with the existing functional molecules of this type, for a specific base sequence occurring on DNA. A hairpin polyamide having an alkylation site via a vinyl linker at the end of a pyrrole-imidazole polyamide. Drugs for inhibiting the expression of a specific gene and anticancer agents containing the above hairpin polyamide.

8 Claims, 9 Drawing Sheets

OTHER PUBLICATIONS

Tao et al., "Highly Cooperative DNA Dialkylation by the Homodimer of Imidazole-Pyrrole Diamide-CPI Conjugate with Vinyl Linker," J. Am. Chem. Soc., vol. 122, pp. 1602-1608, American Chemcial Society (2000).

Bando, Toshikazu et al., "Molecular Design Of A Pyrrole—Imidazole Hairpin Polyamides For Effective DNA Alkylation," Chemistry—A European Journal, 8 (20), pp. 4781-4790, ISSN: 0947-6539, XP008061069 (2002).

Database Caplus [Online] Chemical Abstracts Service, Columbus, Ohio, US; Oyoshi, Takanorl et al., "Regulation of gene expression by sequence-specific alkylating polymide" XP002371001, retrieved from STN, Database accession No. 2002:954878.

Oyoshi, Takanori et al., "Regulation of gene expression by sequence-specific alkylating polyamide," Nucleic Acids Research Supplement, 2 (Twenty-Ninth Symposium on Nucleic Acids Chemistry), 259-260 Coden: Narsce, XP008061071 (2002).

Supplementary Partial European Search Report in corresponding European application No. 03707192 dated Mar. 23, 2006.

* cited by examiner

HAIRPIN POLYAMIDE

TECHNICAL FIELD

The present invention relates to a novel and very useful hairpin pyrrole-imidazole polyamide which inhibits the expression of a specific gene and which has a high anti-cancer activity.

BACKGROUND OF THE INVENTION

In these days, almost all human gene sequences have been analyzed, and a molecule having a specific function directed to a specific certain base sequence draws an attention of many researchers. For example, Dervan et al. discovered that a pyrrole (Py)-imidazole (Im) polyamide oriented in opposite directions was bonded to a minor group of a DNA in a base sequence-specific manner (Bioorg. Med. Chem. 2001, 9, 2215; Curr. Opin. Str. Biol. 1997, 7, 355; J. Am. Chem. Soc. 1997, 119, 7636 and the like). Since such a molecule has a binding constant and a specificity comparable with those of a transcription factor (J. Am. Chem. Soc. 1998, 120, 3534; J. Am. Chem. Soc. 1998, 120, 6219 and the like), it is employed actually in the investigation with regard to the control of a gene expression (Nature, 1997, 387, 202; Proc. Natl. Acad. Sci. USA 1998, 95, 12890 and the like). Nevertheless, the target sequences to which the polyamide is bonded are limited since the control of the gene expression is effected by means of the inhibition of the binding of the transcription factor (J. Am. Chem. Soc., 2000, 122, 4856).

The present inventors have previously developed and applied for patent a hybrid molecule 1 which is obtained by binding a segment A (Du) as an alkylation site of duocarmycin A to a Py-Im polyamide (WO00/15641). This hybrid molecule 1 has an ability of recognizing a sequence and alkylating one site in the DNA fragment of 450 base pairs by Py-Im polyamide (J. Am. Chem. Soc., 1999, 121, 4961). However, the reaction sequence-specific alkylation of a DNA by the molecule 1 takes 1 week or longer to complete, and its reaction efficiency is as low as 7%.

The present inventors also have discovered that an ImPy-LDu86 (wherein L represents a vinyl linker; the same applies to the following description) inserted between the alkylation reaction site and the Py-Im polyamide forms a dimer to react specifically in a sequence of PyG(A/T) CPu at the both chains locating apart by 5 bases from each other (JP 2000-281679; J. Am. Chem. Soc. 2000, 122, 1602). At this time, the inventors made a change into the segment A of Du86 which is a cyclopropylindole (CPI) for the purpose of increasing the stability of the alkylating moiety. This compound was revealed to induce the alkylation in 70% of the ImPyLDu86 employed and allow the reactivity and the efficiency to be increased dramatically as a result of the introduction of the linker.

DISCLOSURE OF THE INVENTION

An objective of the invention is to provide a pyrrole-imidazole polyamide-based functional molecule having further higher DNA-alkylating ability and sequence-recognizing ability on a specific base sequence located on a DNA when compared with a conventional functional molecule of this type.

The invention relates to a hairpin polyamide having an alkylation reaction site via a vinyl linker on the terminal of a pyrrole-imidazole polyamide.

The invention also relates to an agent inhibiting the expression of a specific gene which comprises a hairpin polyamide described above.

Further, the invention relates to an agent having an anti-cancer activity which comprises a hairpin polyamide described above.

1

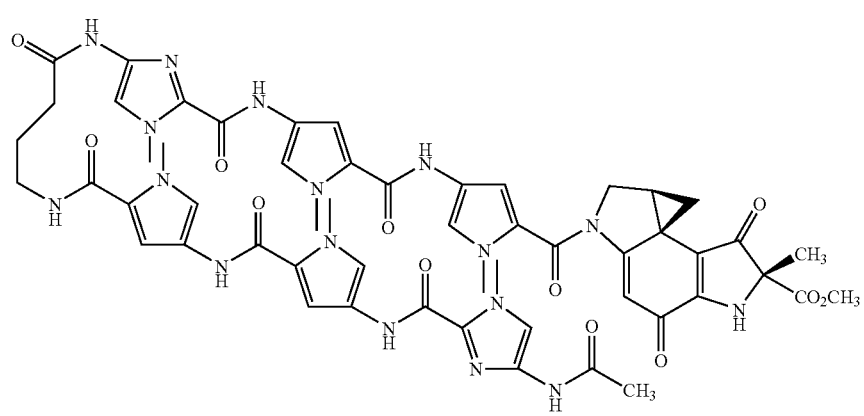

Figure 7:
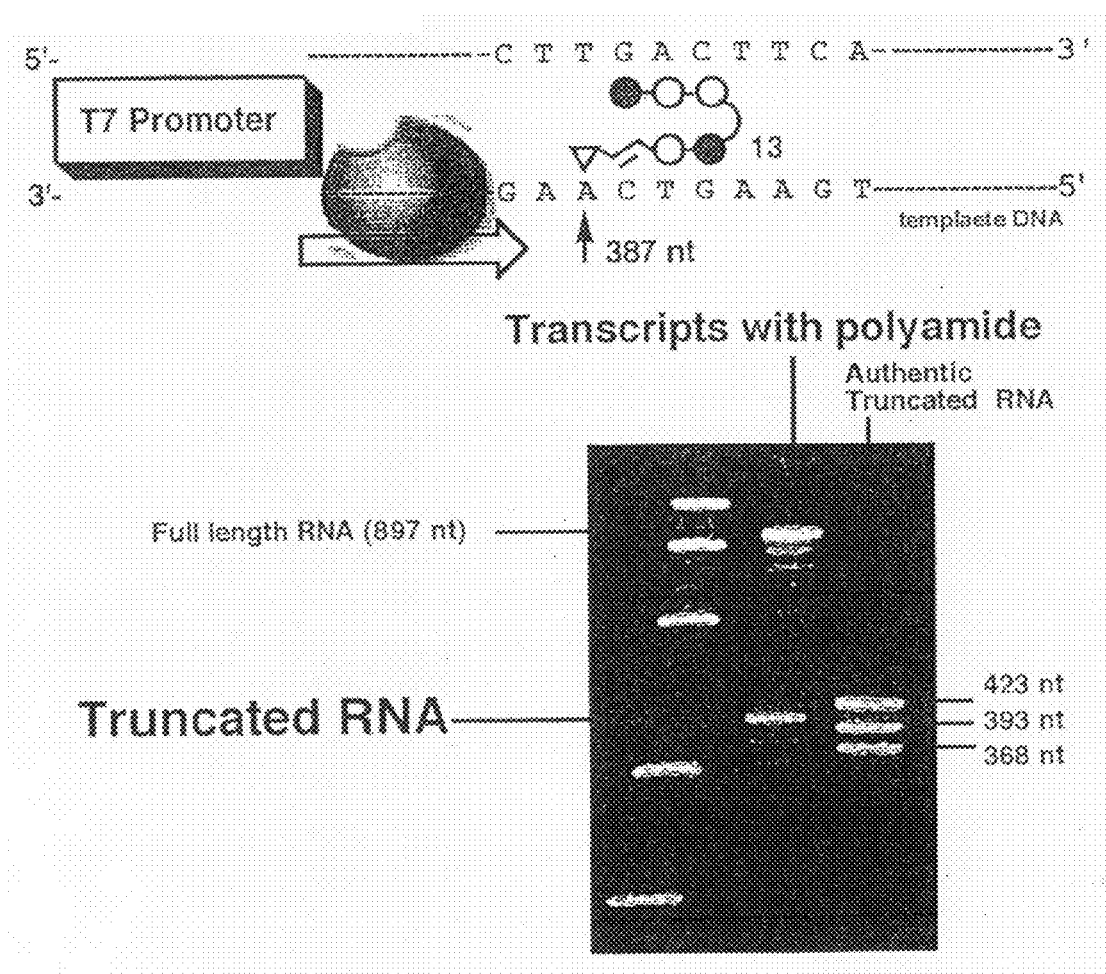

FIG. 7 shows the condition of the inhibition of an mRNA transcription in a coding region by the sequence-specific alkylation by Compound 13.

Figure 8:
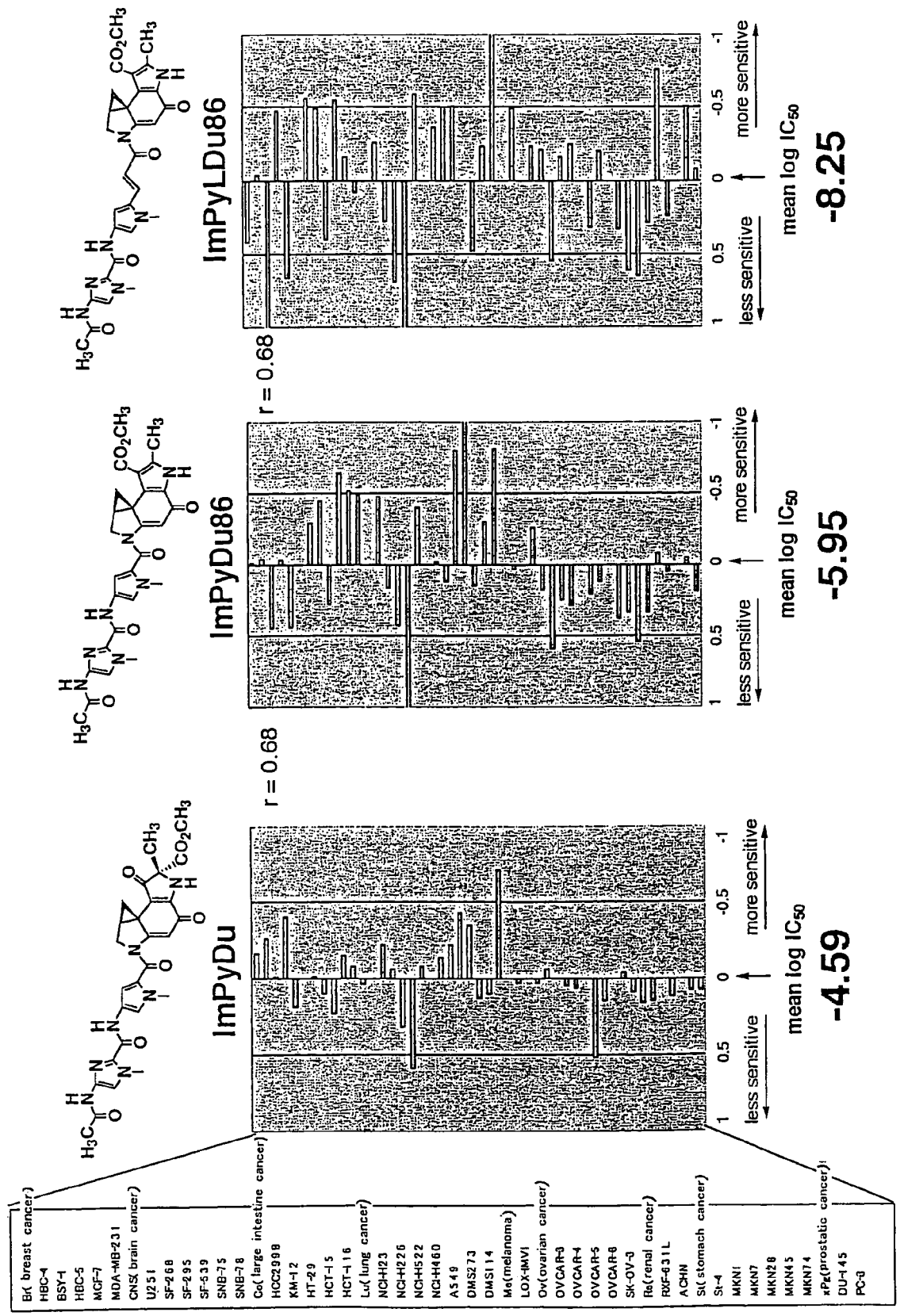

FIG. 8 shows the results of the evaluation of the anti-cancer effect in a human cancer cell panel (39 cancer cell lines).

Figure 9:
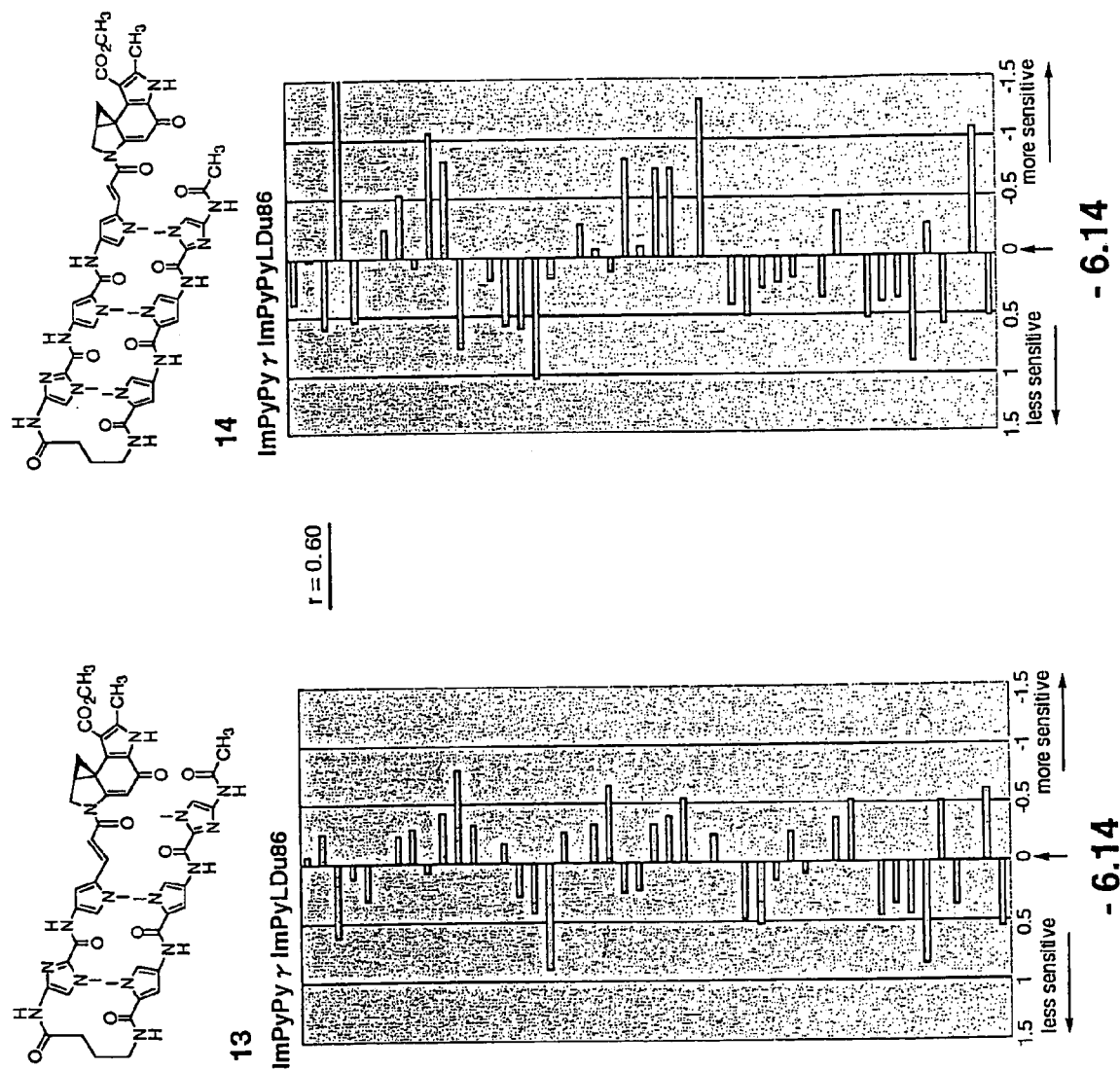

FIG. 9 shows the results of the evaluation of the cytostatic activity of Compounds 13 and 14 on 39 human cancer cell lines.

BEST MODE FOR CARRYING OUT THE INVENTION

A hairpin polyamide of the invention described above may for example be a compound represented by Formula [1]:

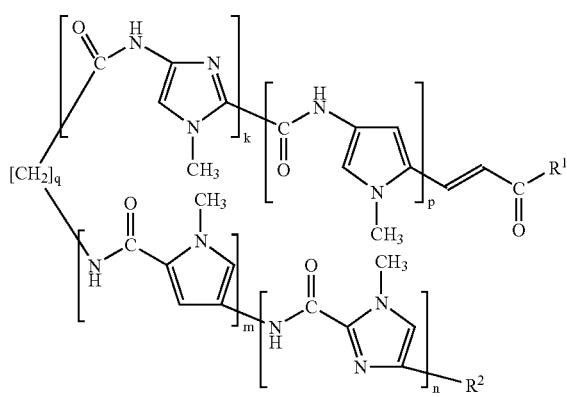

in which $R^1$ is an alkylation reaction site, $R^2$ is a hydrogen, an alkyl group or an acetamide group, and k, p, q, m and n represents a natural number respectively.

In the Formula [1] shown above, the alkylation reaction site represented by $R^1$ may be any group as long as it has both of the alkylating ability and the sequence-recognizing ability on a specific base sequence existing on a DNA, and may for example be a residue of the segment A (Du86) of Du-86 which is a CPI represented by the following structural formula:

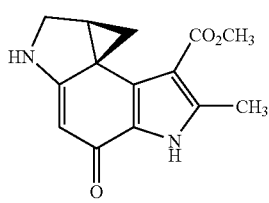

or a residue of 1,2,9,9a-tetrahydrocyclopropa[c]benz[e]-indole-4-one which is a CBI represented by the following structural formula:

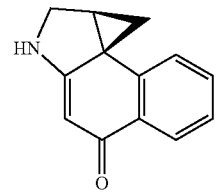

In the Formula [1], the alkyl represented by $R^2$ may for example be a straight or branched lower alkyl group having 1 to 20, preferably 1 to 10, more preferably 1 to 6 carbon atoms, such as methyl, ethyl, n-propyl, isopropyl, n-butyl, isobutyl, t-butyl, pentyl, hexyl groups and the like.

A natural number represented by each of k, p, q, m and n is usually 1 to 10, preferably 1 to 5.

A compound represented by Formula [1] may for example be a compound represented by Formula [2]:

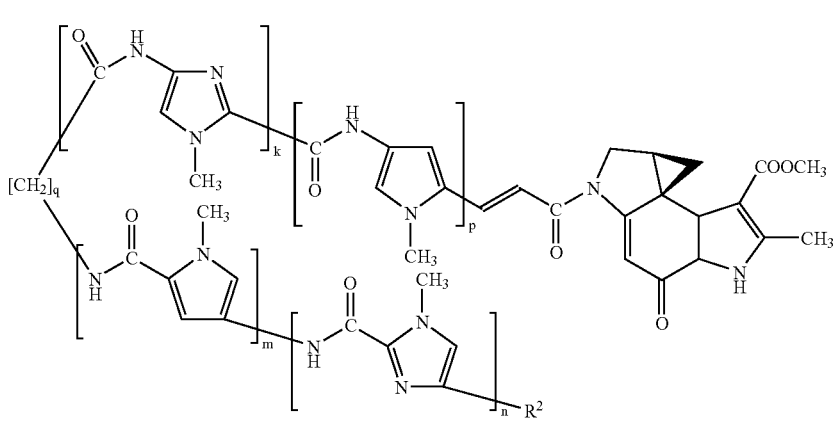

in which $R^2$ is a hydrogen, an alkyl group or an acetamide group, and k, p, q, m and n represents a natural number respectively.

Examples of the compound represented by Formula [2] are a hairpin polyamide represented by the following structural formula:

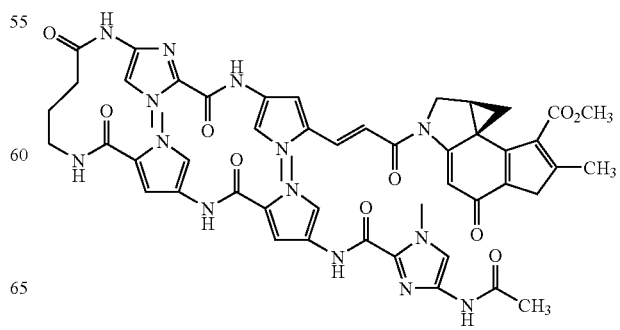

a hairpin polyamide represented by the following structural formula:
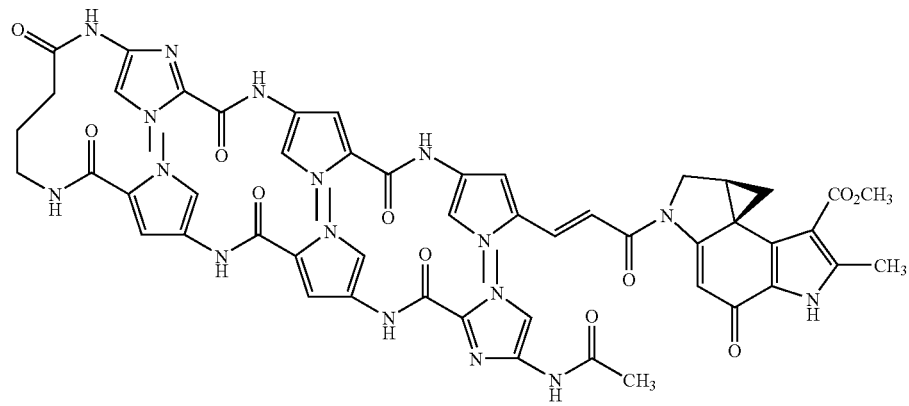
a hairpin polyamide represented by the following structural formula:
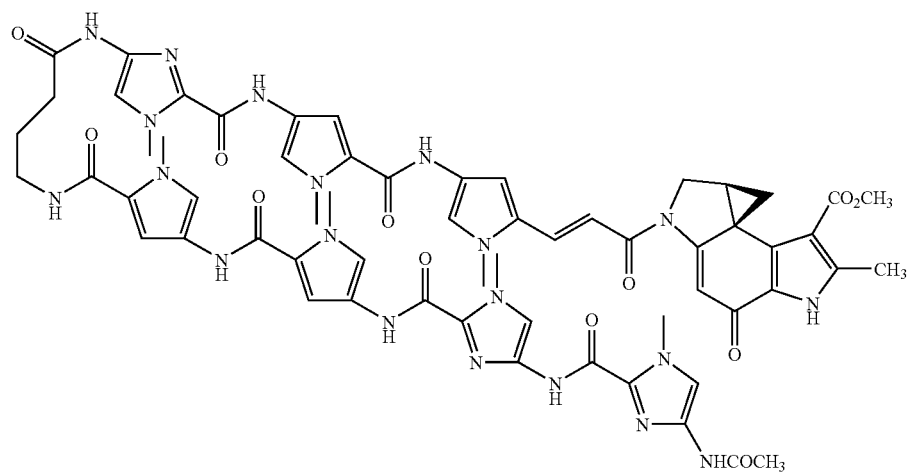
and a hairpin polyamide represented by the following structural formula:

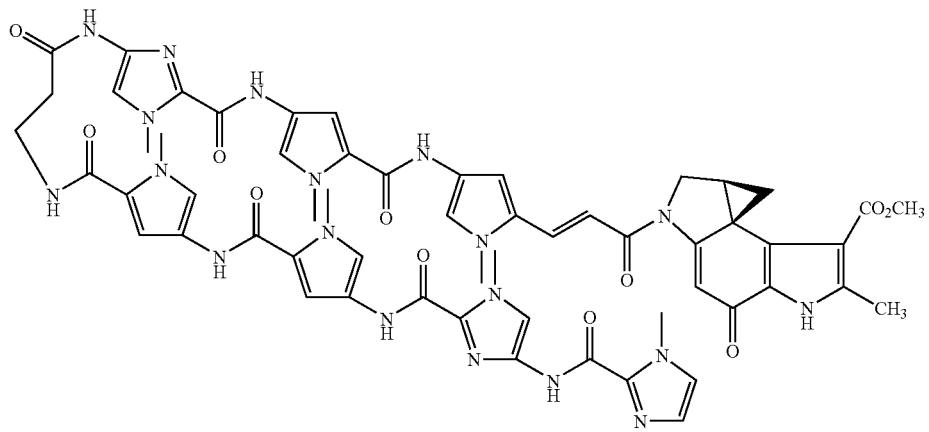
Other examples of the compounds represented by Formula [1] may for example be a compound represented by Formula [3]:
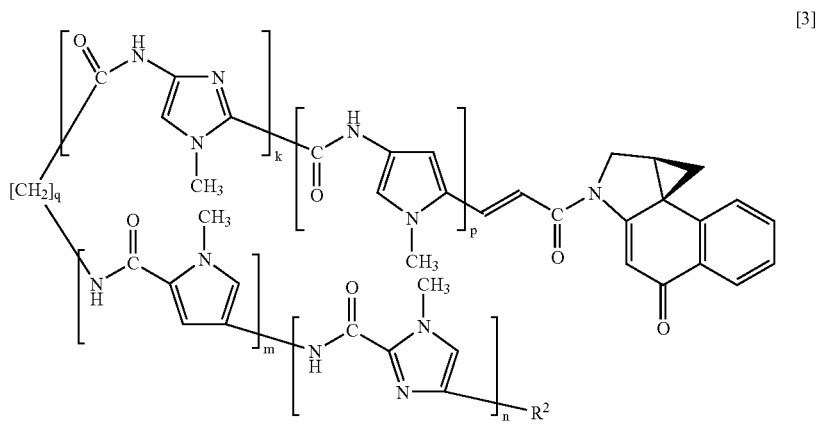
[3]
in which $R^2$ is a hydrogen, an alkyl group or an acetamide group, and k, p, q, m and n represents a natural number respectively.

An example of the compound represented by Formula [3] is a hairpin polyamide represented by the following structural formula:

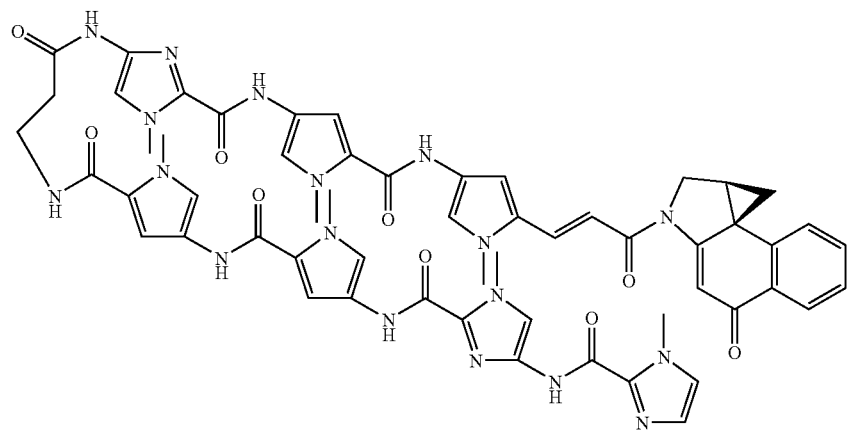

The synthesis of a hairpin polyamide of the invention is outlined in the reaction scheme 1 with referring to Compounds 13 and 14.

In the reaction scheme 1, the synthesis of a conventional hairpin polyamide (Compound 12) employed for the purpose of comparison is also included.

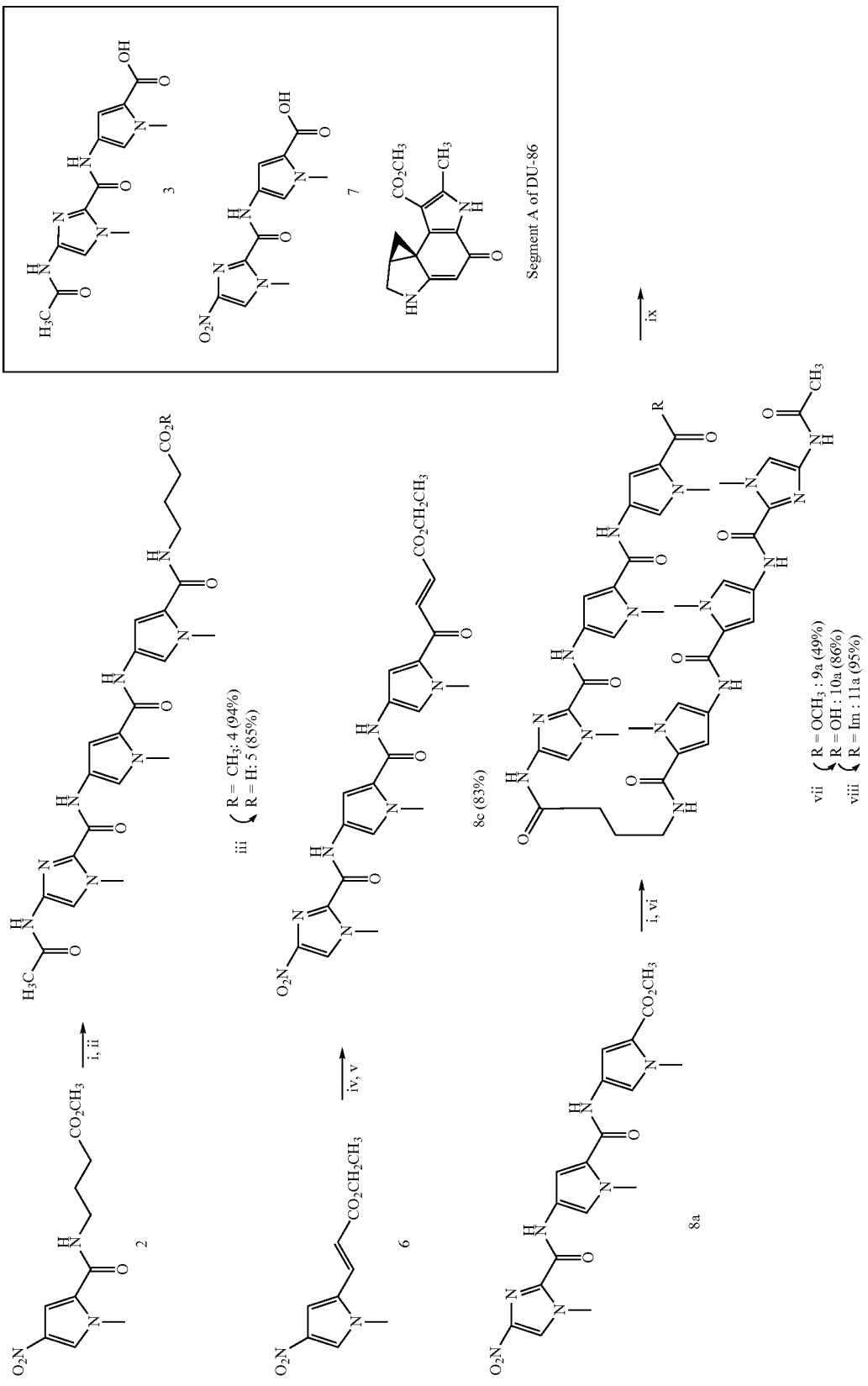

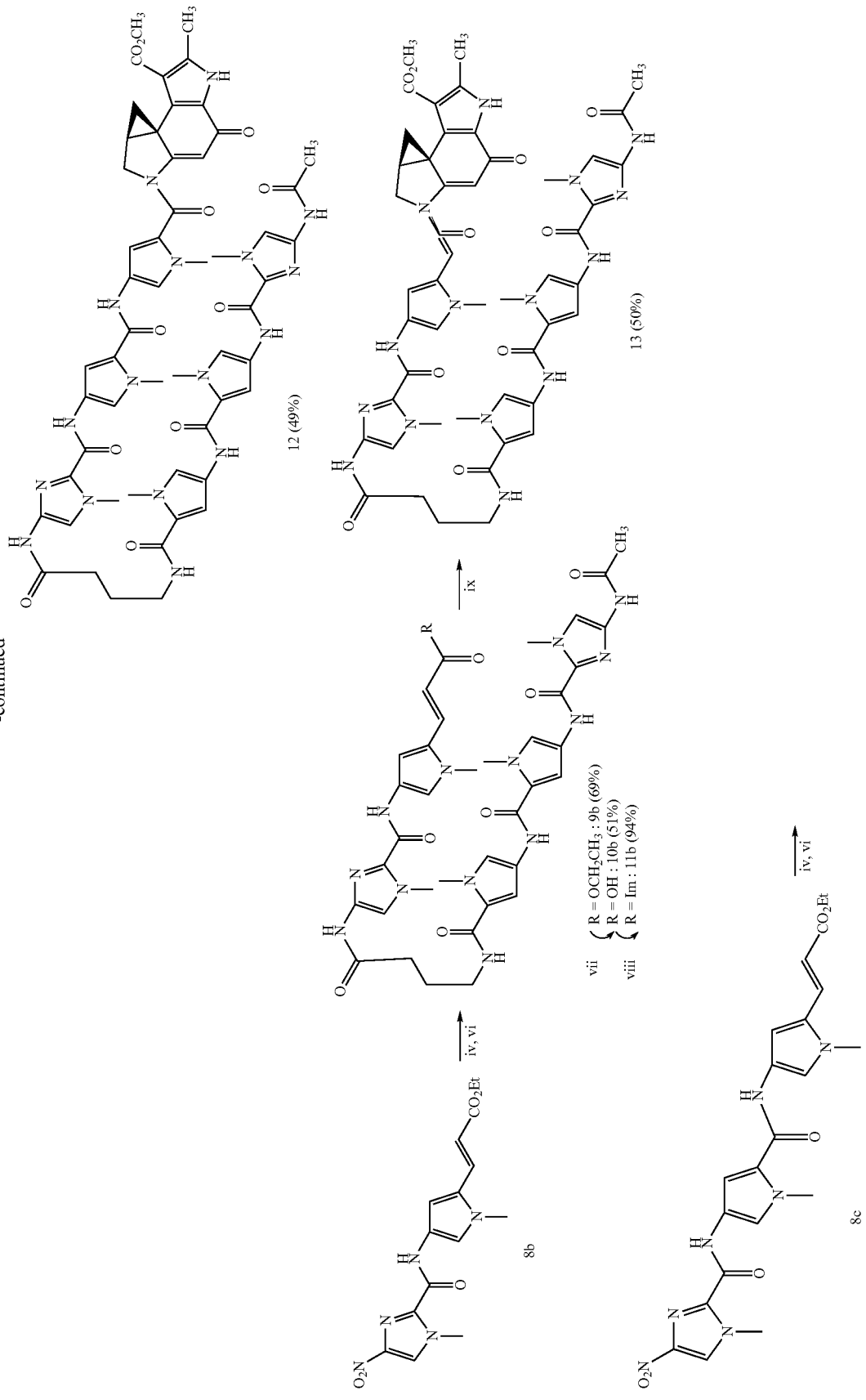

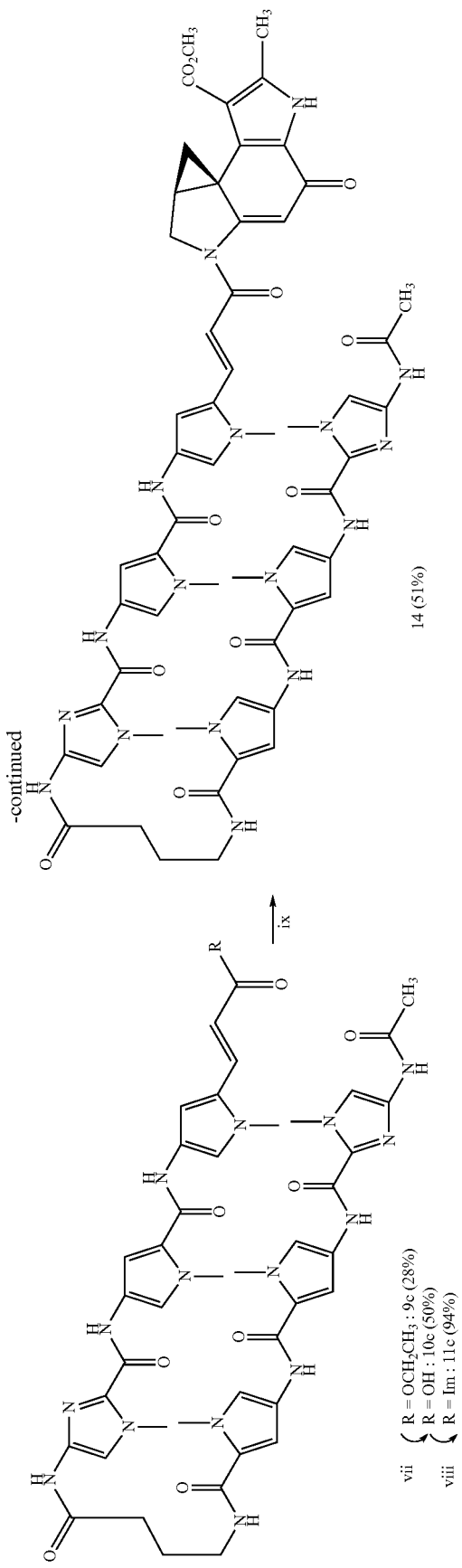
-continued
14 (51%)
vii { R = OCH$_2$CH$_3$ ; 9c (28%)
viii { R = OH : 10c (50%)
       R = Im : 11c (94%)
condition: (i) Pd-C, H$_2$, MeOH-AcOEt; (ii) 3, FDPP, $^i$Pr$_2$NEt, DMF; (iii) NaOH, H$_2$O; (iv) Pd-C, NaBH$_4$, MeOH-AcOEt; (v) 7, FDPP, $^i$Pr$_2$NEt, DMF; (vi) 5, FDPP, $^i$Pr$_2$NEt, DMF; (vii) DBU, H$_2$O; (viii) 1,1'-carbonyldiimidazole, DMF; (ix) Segment A of DU-86, NaH, DMF.

Thus, the coupling of Compounds 2 and 3 was conducted using a commercially available FDPP to synthesize a triamide 4, which is then hydrolyzed to yield a carboxylic acid 5, which was used as a common part corresponding to the half on the side of the N terminals of Compounds 12 to 14. As a result of the coupling of Compounds 8a-c with Compound 5, whereby synthesizing hairpin esters 9a-c. As the alkylation site, the segment A of DU86 which is stable under the condition of the coupling with the polyamide moiety was used to synthesize Compounds 12 to 14. The final compound was aliquoted and purified by an HPLC, and identified for its structure by NMR and an electrospray mass spectrum.

Long Chain DNA (400 bp)-Alkylating Ability

Figure 1:
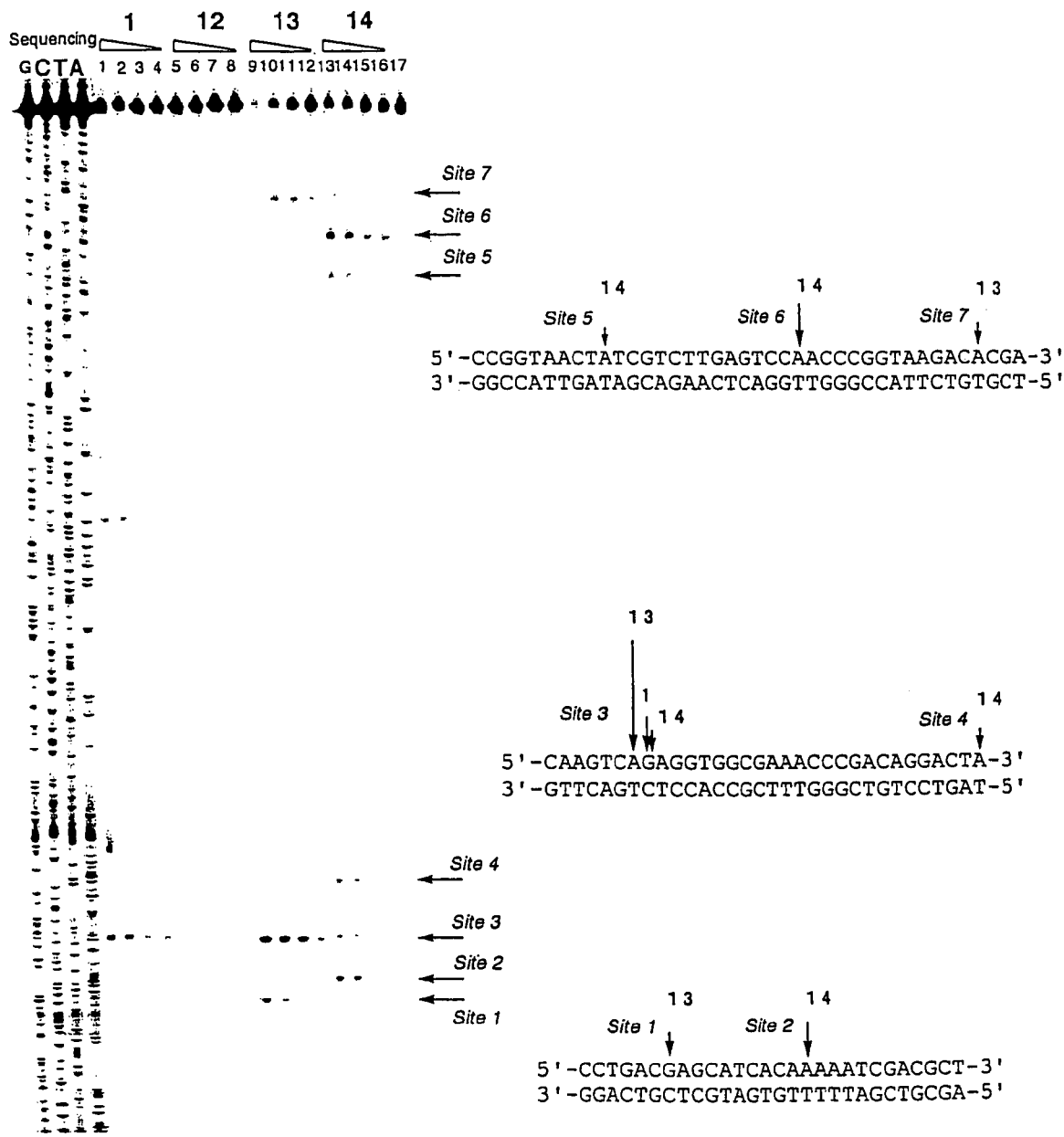
FIG. 1 shows the comparison of the DNA base sequence-specific alkylation reaction by Compounds 1, 12 to 14.

The reaction of the hairpin polyamides 1 and 12 to 14 with a DNA was investigated using a long chain DNA (pUC-I'). The alkylation reaction was continued for 24 hours and a sequence gel electrophoresis was conducted for the analysis. The results are shown in FIG. 1.

ImPyPy-γ-ImPyPyDu (1) employed as a reference control reacted selectively at G in the 5'-GTCAG-3' sequence in Site 3. On the other hand, the alkylation of ImPyPy-γ-ImPy-PyDu86 (12) was not observed at 100 nM to 12.5 nM (lanes 5 to 8). Even when the concentration was elevated to 10 µM, the DNA never disappeared, and showed no occurrence of the alkylation. These findings suggest that the Du has a higher reactivity than the Du86. On the other hand, ImPyPy-γ-ImPyLDu86 (13) formed by deleting one pyrrole molecule and inserting a vinyl linker exhibited a more excellent alkylating ability, and not only reacted at A in the GTCAG sequence of the site 3 (Lane 9 to 12) but also resulted in the disappearance of almost all starting DNA at 100 nM (lane 9). In addition, while ImPyPy-γ-ImPyPyLDu86 (14) formed by inserting a vinyl linker to the ImPyPy-γ-ImPyPy exhibited a slightly reduced reactivity when compared with Compound 13, the alkylation occurred at the match sites 7 and 4 whose predominantly alkylated base sequences were different from G of the GTCAG sequence at the site 3 and also at the mismatch site 2, which exhibits the sequence specificity is different from that of Compound 1 (Lanes 13 to 16). These results were considered to be due to an increased freedom near the Du86. In the description made above or below, a -γ- means a γ-aminobutyric acid residue.

Figure 2:
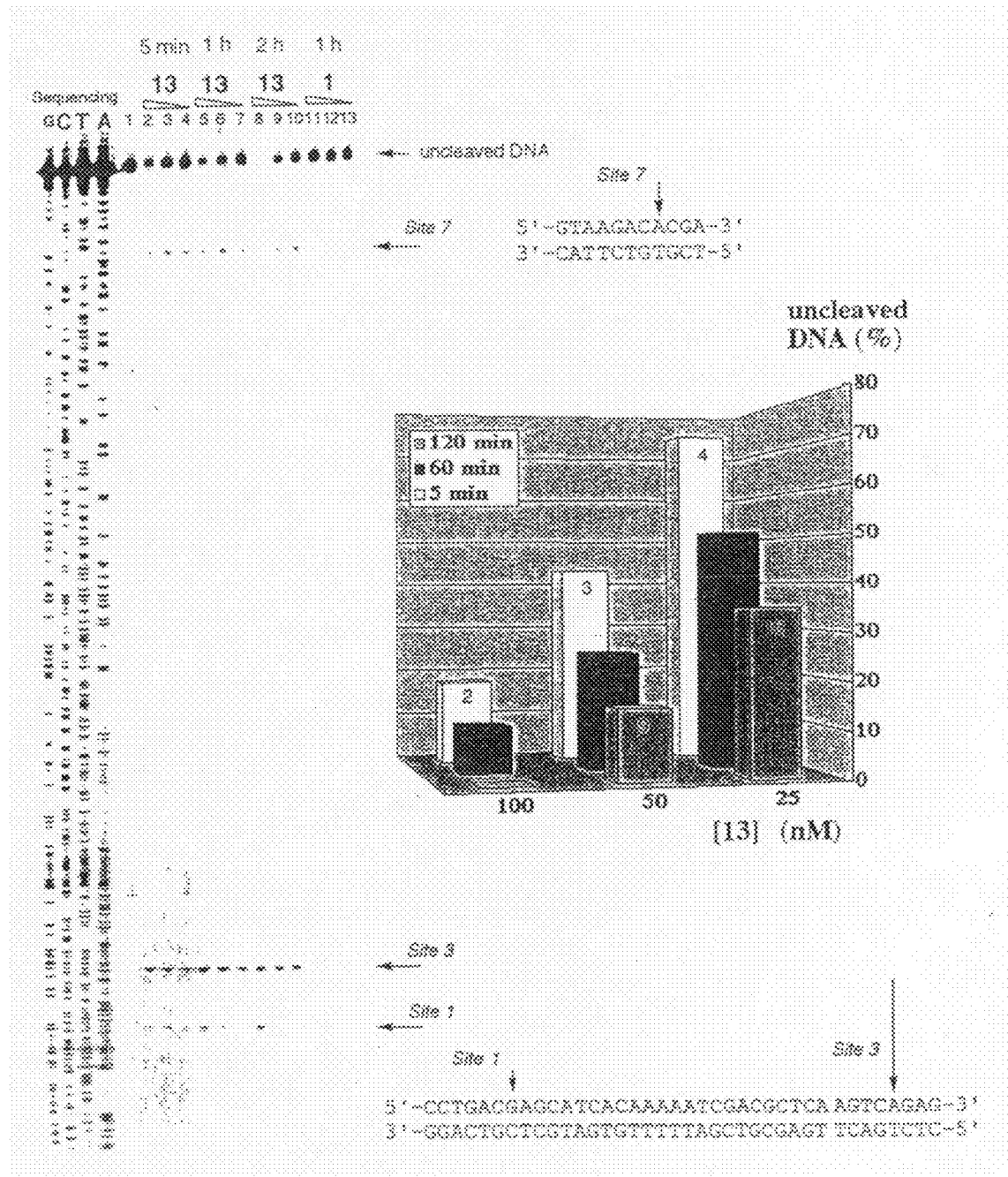
FIG. 2 shows the results of the pharmacokinetic evaluation of the DNA-alkylating ability of Compounds 1 and 13.

In order to investigate the difference in the reactivity between Compounds 1 and 13 in more detail, the alkylation within a short period was analyzed. Interestingly, the results indicated that Compound 13 caused the alkylation even in the reaction for a time period as short as 5 minutes while Compound 1 caused no reaction even after one hour. These findings indicate that Compound 13 had a sequence-specific DNA alkylation velocity which was increased dramatically against DNA when compared with Compound 1 (FIG. 2).

Short Chain DNA (10 bp) Alkylation

Figure 3:
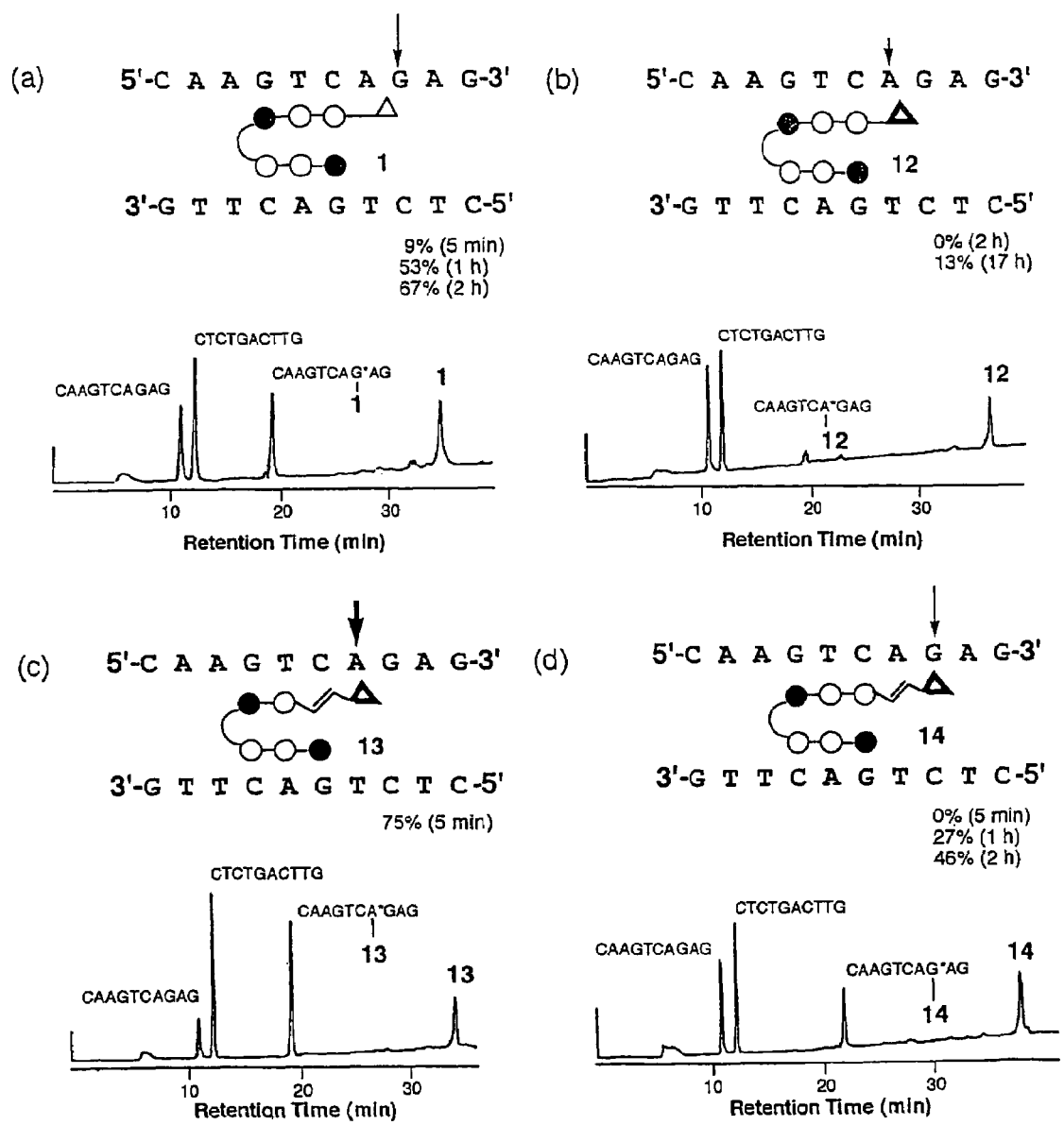
FIG. 3 shows the results of the evaluation of the sequence-specific alkylation reaction by Compounds 1, 12 to 14 toward a short chain DNA.

In order to clarify the reactive base site in an alkylation site, the alkylation with Polyamides 12, 13 and 14 was investigated by an HPLC using DNA oligomers 5'-CAAGTCA-GAG/5'-CTCTGACTTG as substrates. The results are shown in FIG. 3. While the polyamides exhibited various reactivities, all exhibited the peaks possibly attributable to the alkylated forms as the reaction was advanced. Also by decomposing the oligomers by heating and investigating the degradation products of the oligomers by the method which the inventors reported previously (Tetrahedron Lett. 1990, 31, 7197; Tetrahedron Lett. 1993, 34, 2179 and the like), it was proven that the alkylation reaction occurred at the site indicated by an arrow. Also with regard to the reactivity on the oligomers, the reactivity of Compound 12 was proven to be extremely poorer when compared with Compound 1 (13% after 17 hours, FIG. 3). These findings may be attributable to the difference in the reactivity between the Du and the Du86 similarly to the reactivity on the long chain DNA. On the contrary, Compound 13 exhibited a dramatically increased reactivity (75% after 5 minutes). This indicates that the DNA-alkylating ability is influenced by the position in the DNA minor group more significantly rather than by the reactivity of the alkylation site (Du86). In view of only the reactivity on the short chain DNA, Compound 14 (46% after 2 hours) was almost equivalent to Compound 1 and poorer than Compound 13.

Based on the results described above, a molecular design like Compound 13, i.e., the presence of the vinyl group between the imidazole-pyrrole hairpin polyamide and the CPI alkylator, was proven to contribute greatly to the dramatic increase in the DNA-alkylating ability. It was also proven that the combination of the vinyl group with the segment A functioned efficiently also for the base sequence recognition by the DNA-alkylating agent. The hairpin polyamides 13 and 14 synthesized here are the base sequence-specific alkylating agent having high DNA-alkylating abilities, and the results of the investigation with regard to the gene expression control and the anti-cytostatic activity on a cancer cell are described below.

Molecule Design of Sequence-Specific Alkylating Agent having Wider Recognizable Base Sequence As a functional molecule having a wider span of the recognizable sequence, an AcImImPyPy-γ-ImPyPyLDu86 (15) formed by adding an imidazole ring to the N terminal of Compound 14 was designed. Also for verifying the effect of the N terminal on the alkylation, an acetyl group was deleted to design an ImImPyPy-γ-ImPyPyLDu86 (16). The synthetic method was similar to the scheme 1, and the carboxylic acids 17 and 18 and the amine form 19 were subjected to the coupling using FDPP to synthesize Compound 20, and Compounds 15 and 16 were yielded after the coupling with Compound 8c. The final compound was aliquoted and purified by an HPLC, and identified for its structure by an NMR and an electrospray mass spectrum (scheme 2).

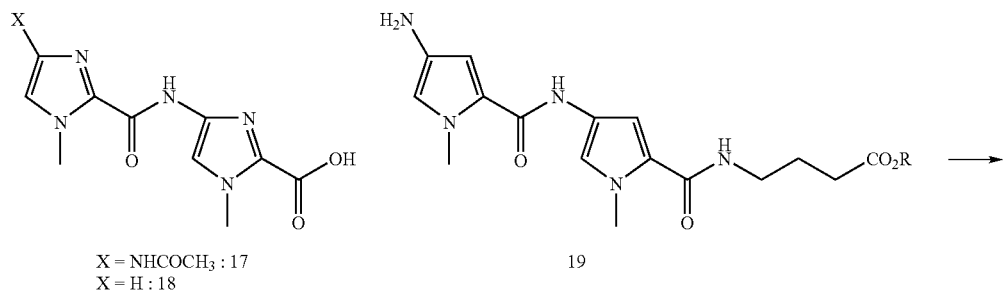
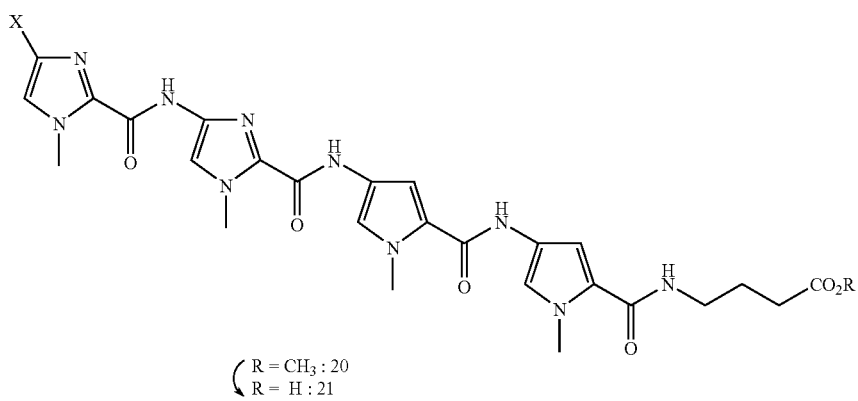
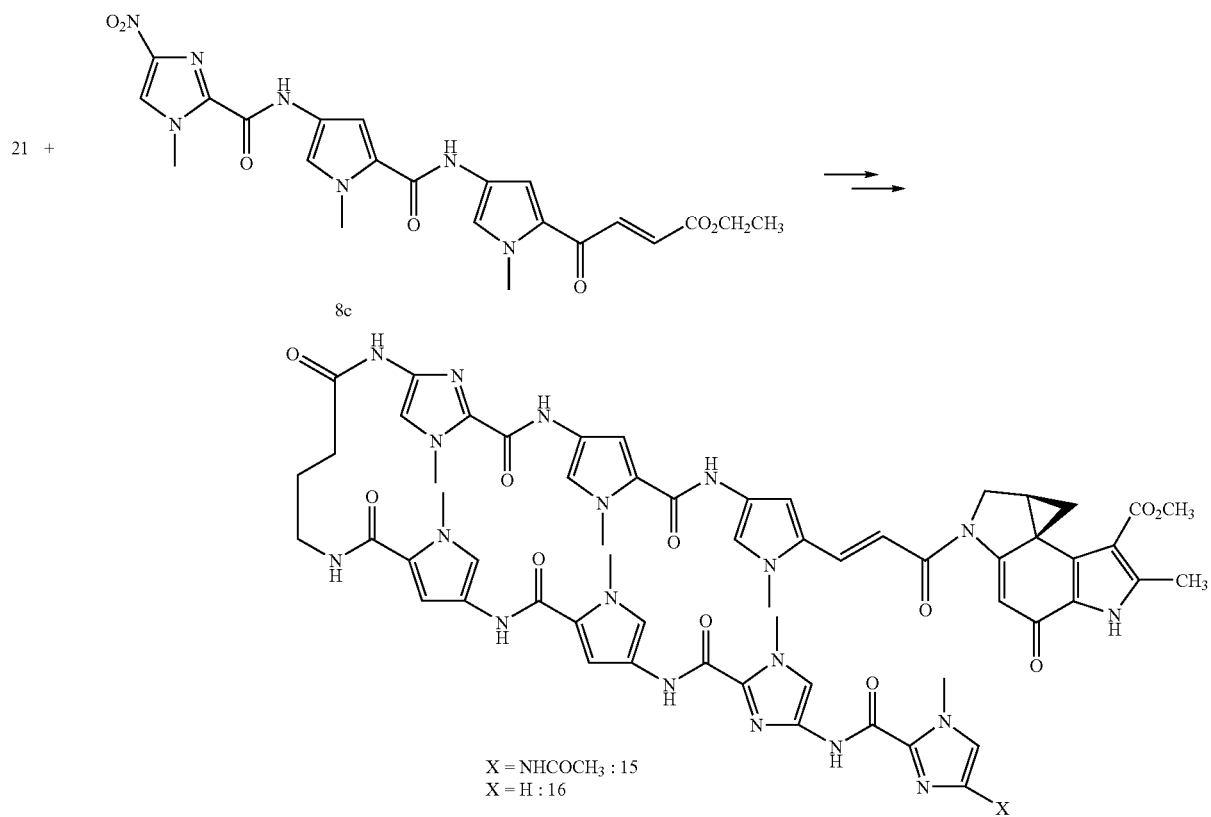

Figure 4:
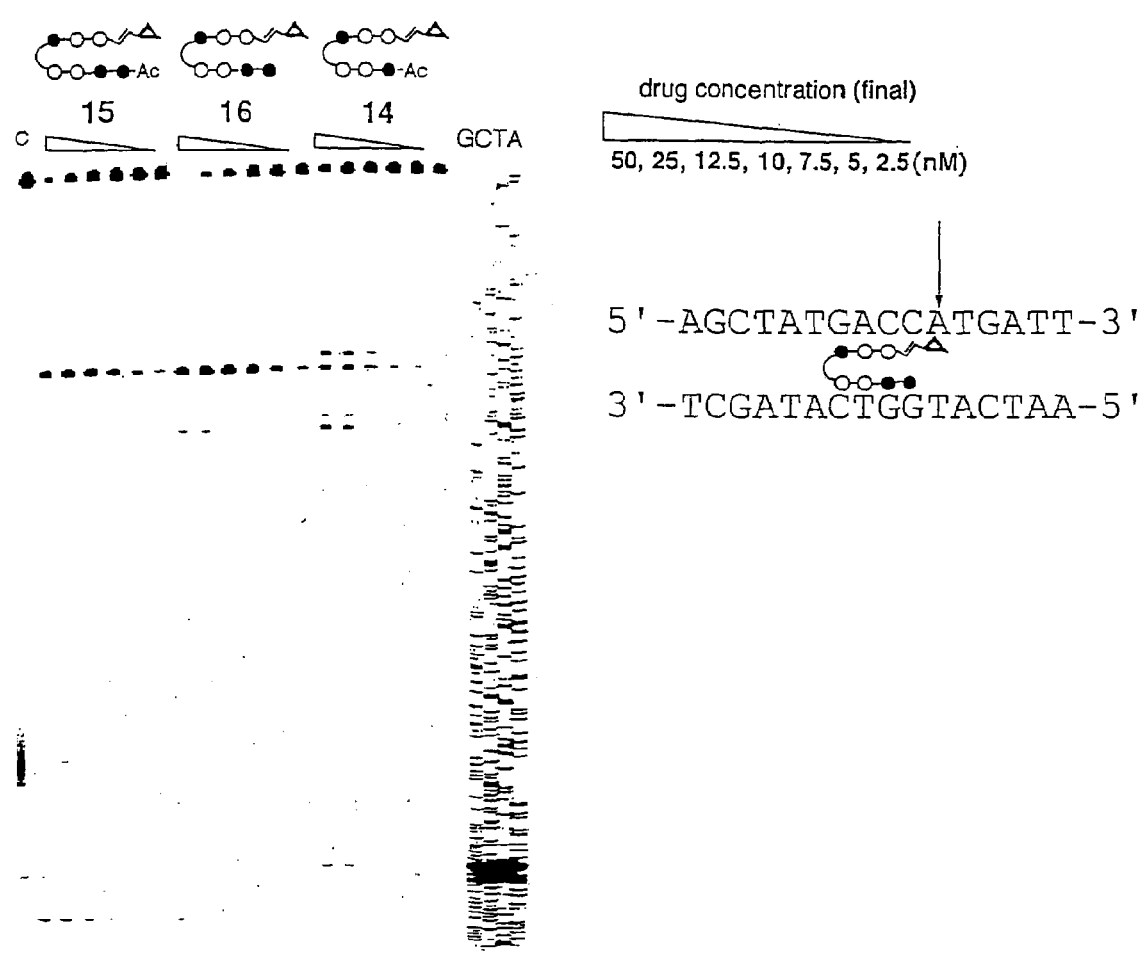
FIG. 4 shows the results of the analysis of the base sequence-specific DNA alkylation reaction of Compounds 14 to 16 with the 5'-TGACCA-3' sequence.

For the purpose of comparing the hairpin polyamides 14, 15 and 16, the DNA alkylation reaction employing a long chain DNA (pUC-II) was conducted. The reaction was continued for 24 hours, and analyzed by a sequence gel electrophoresis, and the results indicated that the sequence-specific alkylation was observed at 5'-TGACCA-3' at respective nM concentrations (FIG. 4).

Interestingly, Compound 14 also caused the alkylation of a match sequence 5'-TGACCA-3', but its reactivity is far lower than those of Compounds 15 and 16, and also caused the alkylation of a mismatch sequence. It is clear that the freedom near the Du86 resulted in a reduction in the sequence-recognizing ability. On the other hand, there was almost no influence by the removal of the N terminal acetyl group. The molecular designs of Compounds 15 and 16 contain the sequence-recognizing ability based on the Im-Py recognition rule, and the recognizable base sequence can be altered by changing the position of the imidazole-pyrrole. Such a sequence-specific alkylating agent having both of a base sequence-recognizing ability and a high DNA-alkylating ability has not been identified heretofore.

Molecule Design of Sequence-Specific Alkylating Agent for Higher Practicability

Each of the functional molecules 13, 14, 15 and 16 developed by the inventors as described above is an ideal sequence-specific alkylating agent having both of a highly excellent base sequence-recognizing ability and a high DNA-alkylating ability expressed at a level of nM concentration. Moreover, by altering the position of the imidazole-pyrrole, the recognizable sequence can be changed. Nevertheless, any of these compound is somewhat problematic when intended to be produced on a large scale since its DNA-alkylating site employs the segment A derived from duocarmycin $B_2$ which is a natural product.

Figure 5:
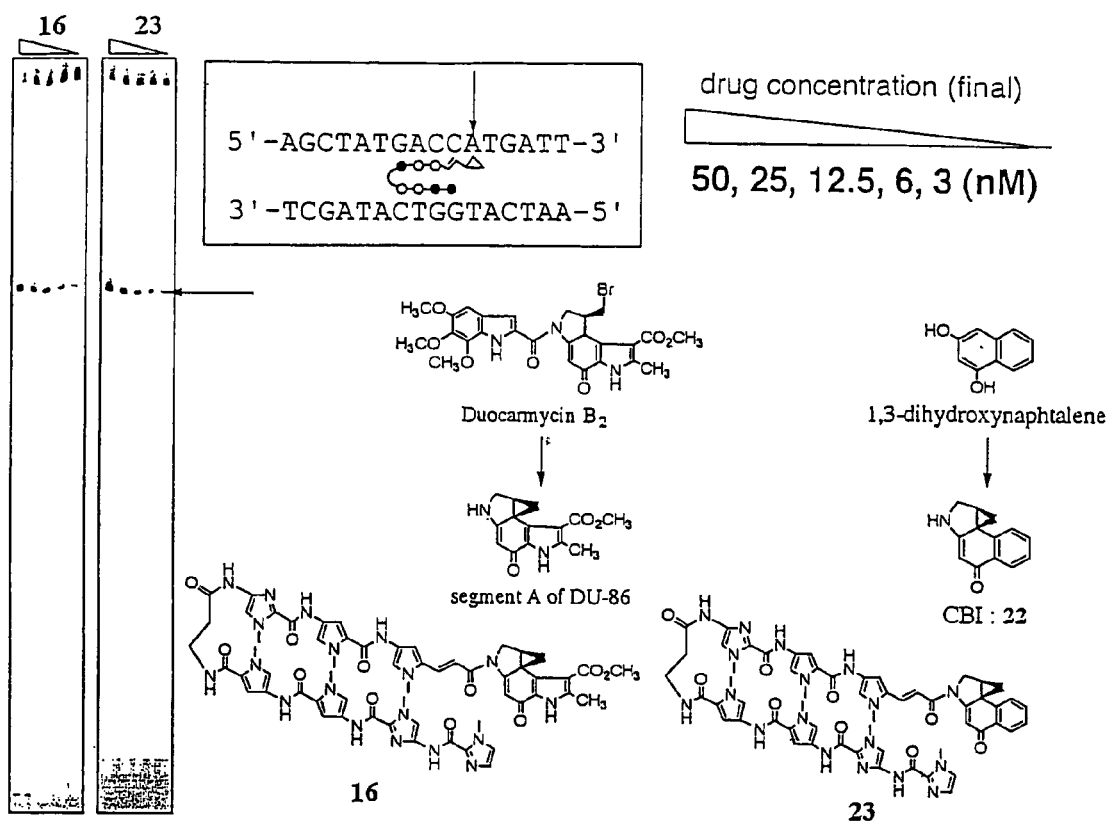
FIG. 5 shows the comparison of the base sequence-specific DNA-alkylating ability of Compounds 16 and 23.

With this regard, the inventors considered that this problem can be solved by replacing the Du86 with CBI: 1,2,9,9a-tetrahydrocyclopropa[c]benz[e]indole-4-one (22), the method for synthesizing which had already been reported by Boger et al. (J. Org. Chem. 1992, 57, 2873; J. Org. Chem. 1995, 60, 1271 and the like). The benefit of using CBI includes the ability of using commercially available 1,3-dihydroxynaphthalene as a starting material and the ability of providing both enantiomers by an optical resolution. Accordingly, the inventors newly synthesized Compound 23 by replacing the Du86 part of Compound 16 with CBI. Then the inventors evaluated the DNA-alkylating ability using a long chain DNA (pUC-II). The results are shown in FIG. 5.

As a result, CBI was found to be capable of effecting a sequence-specific alkylation which is comparable with that of the segment A of the Du86. This replacement with CBI is considered to be applicable to the sequence-specific alkylating agent the inventors have been developed.

The inventors found to bind an already existing Im-Py hairpin polyamide to CBI via a vinyl linker. This vinyl linker-mediated binding gives an optimized molecular design, which is a significant factor for obtaining a sequence-specific alkylating agent. These findings allow the sequence-specific alkylating agent developed by the inventors to be used practically and widely.

Application of Py-Im Polyamide as Base Sequence-Specific Alkylating Agent (i) Possible Utility as Gene Expression-Controlling Tool—for Developing a Novel Gene Knockout Method A method for controlling the expression of a certain gene artificially may for example be an antisense method in which a DNA derivative complementary with an mRNA which is a gene transcription product is administered to inhibit the translation into a protein and a lipozyme method in which the mRNA is cleaved in a sequence-selective manner, with the former being brought into a practical use in the form of an eyedrop formulation against a cytomegalovirus in HIV patients. A method for inhibiting the gene transcription steps may for example be an anti-gene method for forming a triple-stranded chain with the double-stranded DNA targeting an oligonucleotide derivative, for which several venture companies have been established in the United States. However, this method has not been brought into a practical use since the targeted base sequence is limited to the region in which A and G are aligned consecutively and also since an oligonucleotide is difficult to migrate into a nucleus.

Figure 6:
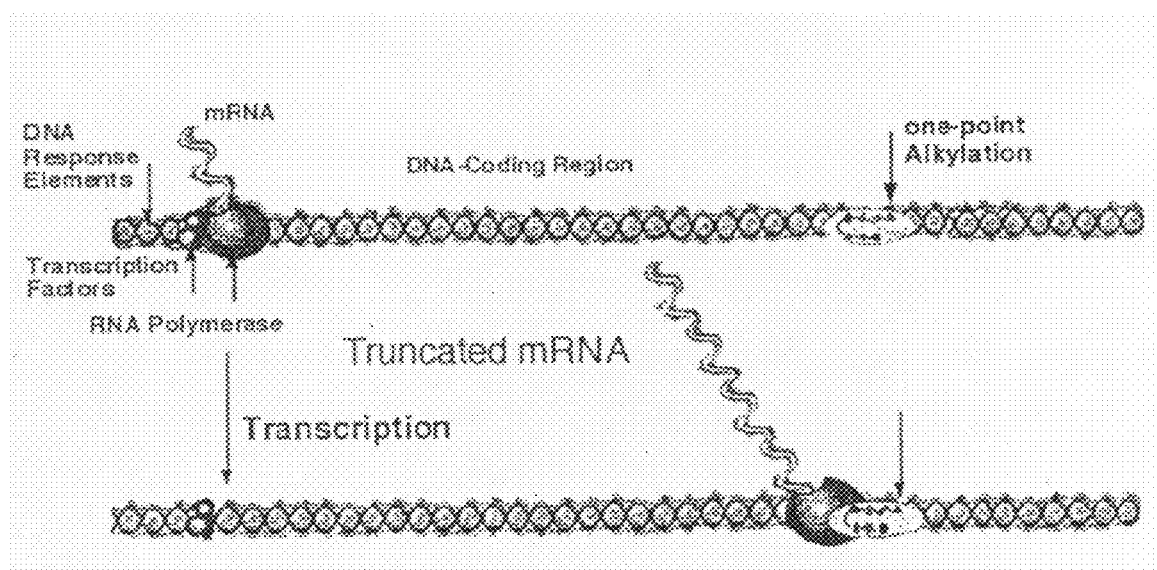
FIG. 6 shows the results of the investigation of the gene expression control in a coding region.

In contrast, a Py-Im polyamide enables any selection of the targeted base sequence and exhibits very excellent permeation into the cell membrane or nuclear membrane, and thus is assumed to be an efficient molecule with potential capable of controlling the gene expression. In fact, Dervan et al. reported that a pyrrole (Py)-imidazole (Im) polyamide was used to control the expression of a gene. Nevertheless, the gene expression control by Dervan et al. is effected by means of the inhibition of the transcription factor binding, which practically limits the target sequences to which the polyamide is bound. Since the Py-Im polyamide having an alkylating ability is bound to a DNA in a sequence-specific manner, it is considered to be capable of controlling the expression of a certain gene efficiently not only in a regulatory region but also in a protein-encoding region. Accordingly, such a molecule is assumed to be utilizable for investigating the functions of an unknown gene as a knockout gene method required in this post-genome period as well as for producing a tailor-made pharmaceutical. Since the Py-Im polyamide having an alkylating ability is bound covalently to a DNA in a sequence-specific manner, it is considered to be possible to control efficiently even in the region encoding the expression of a certain gene protein (FIG. 6). This means the possibility of selecting any sequence as a target outside of the regulatory region in which the targets mostly resemble each other.

Such a benefit gives a possibility of being used as a novel anti-cancer agent based on the molecular biology of a disease. Thus, a method employing as a target a gene known to play an important role as an anti-cancer agent in a cell, such as ras oncogene, cell cycle-regulating E2F gene, telomere region or telomerase gene may be included.

While an experiment using a GFP protein expression coding region together with a T7 promoter and a T7 polymerase is conducted currently as an early stage experiment, an mRNA produced by the transcription inhibition of a polymerase attributable to the sequence-specific alkylation of Compound 13 effected on the adenine in the 387 nt position in this coding region was observed successfully (FIG. 7). The condition of the experiment has not been established yet, and a further detailed analysis of the transcription inhibition mechanism is required. Nevertheless, these results indicated for the first time that a sequence-specific alkylating agent has an ability of inhibiting the transcription specifically in a coding region, and are considered to have a great significance. It leads to a breakthrough toward the development of a novel knockout gene method.

(ii) Effect of Sequence-Specific Alkylating Agent on Anti-Cytostatic Effect—for Development of Tailor-Made Anti-Cancer Agent As a result of the investigation of the cytostatic activity of various Py-Im polyamides synthesized by the inventors each having a sequence-specific alkylating ability on 39 human cultured cancer cell lines (the cytostatic activity on 39 types of human cultured cancer cell lines was evaluated by T. Yamori in Cancer Chemotherapy Center of Japanese Foundation for Cancer Research), several interesting facts were revealed. The first is the proportional relationship between the DNA-alkylating ability and the cytostatic activity (FIG. 8). For example, the mean $IC_{50}$ values of ImPyDu (−4.59), ImPyDu86 (−5.95) and ImPyLDu86 (−8.25) were reduced gradually as the DNA-alkylating ability was increased. It is especially noteworthy that a dramatic increase in the cytostatic activity due to the location of the vinyl linker between the imidazole-pyrrole polyamide and the Du86 was observed also when using an analogous sequence-specific alkylating agent (PyPyLDu86, PyPyPyLDu86, ImPyPyLDu86).

A further interesting result was obtained when comparing the fingerprint patterns indicating the cytostatic activity of the hairpin sequence-specific alkylating agents ImPyPy-γ-ImPy-LDu 36 (13) and ImPyPy-γ-ImPyPyLDu 36 (14) (FIG. 9). In general, a high correlation coefficient (r=0.75 to 1.0) is known to be obtained when comparing the fingerprint patterns between the drugs whose action mechanisms are analogous to each other, and in fact an extremely high analogy was observed among a DNA intercalator, doxorubicin, daunorubicin and epirubicin. However, Compounds 13 and 14 exhibited a considerably low correlation of the fingerprint patterns (r=0.60) in spite of being the same DNA minor group and having the same reaction mechanism by which the N3 position of adenine and guanine is alkylated. The influence on the cytostatic activity attributable only to the difference in the base sequence-recognizing ability in spite of the analogy in the structure as observed with these Compound 13 and 14 has never been reported, and thus is one of the most important findings. These results mean that the anti-cytostatic activity can be altered by imparting an alkylating agent with a sequence selectivity and suggest that a way to a novel anti-cancer agent or gene therapy will be provided.

DNA-alkylating agents are referred to as first generation anti-cancer agents and many agents such as mitomycin, cisplatin, nitrogen mustard, cyclophosphamide have been developed and are used clinically in these days. Nevertheless, they involve problems which are difficult to be solved such as severe side effects on normal cells, and their development is now retarded. Accordingly, a metabolism antagonist such as methotrexate or 5-fluorouracil, a topoisomerase inhibitor such as camptotecin and an anti-cancer agent targeting tubulin rather than DNA such as taxol are now in the mainstream of the development. By imparting a DNA-alkylating agent with a DNA base sequence specificity whereby selectively controlling the expression of a specific gene, a way to the development of a tailor-made anti-cancer agent having no side effects will be provided.

The entire description in Japanese Application number 2002-063608 is herein incorporated accordingly.

EXAMPLES

The invention is further described in the following EXAMPLES which are not intended to restrict the invention.

Example 1

Synthesis of 5'-Texas Red-Labeled 450 Base Pair DNA

A DNA fragment (pUC-I') was synthesized by a PCR method using pUC 18 as a template together with a 5'-texas red-labeled 20 base pair primer: 5'-AGAATCAGGG-GATAACGCAG-3' (pUC 18 forward, 780-799) and 20 base pair primer: 5'-TTACCAGTGGCTGCTGCCAG-3' (pUC18 reverse, 1459-1478). The resultant DNA fragments were purified by filtration through a Suprec-02, and then examined for the UV absorption to determine the respective concentrations.

A DNA fragment (pUC-II) was synthesized by a PCR method using pUC 18 as a template together with a 5'-texas red-labeled 21 base pair primer: 5'-TGCTGGCCTTTTGCT-CACATG-3' (pUC 18 reverse, 1861-1881) and 18 base pair primer: 5'-TGTAAAACGACGGCCAGT-3' (pUC18 forward, 378-395). The resultant DNA fragments were purified by filtration through a Suprec-02, and then examined for the UV absorption to determine the respective concentrations.

Example 2

Polyacrylamide Gel Electrophoresis Analysis

To 10 μl in total of 5 mM sodium phosphate buffer (pH7.0), a standard reaction solution containing 10 nM of the DNA fragment (pUC-I') whose 5'-terminal had been labeled with the texas red, 10% (v/v) DMF and an agent at the concentration indicated in FIG. 1 was added in a microcentrifugation tube (Eppendorf) and allowed to stand for 24 hours at 23° C.

[Lanes 1-4, 100, 50, 25, 12.5 nM (1); Lanes 5-8, 100, 50, 25, 12.5 nM (12); Lanes 9-12, 100, 50, 25, 12.5 nM (13); Lanes 13-16, 100, 50, 25, 12.5 nM (14); Lane 17, DNA control].

A bovine thymus DNA (1 mM, 1 μL) was added for quenching, and the mixture was shaken for 5 minutes at 90° C. The DNA obtained by centrifugation under reduced pressure was combined with 8 μl of a loading color (solution of *FUGENE* Red in DMF) and dissolved, and then shaken for 20 minutes at 94° C. Immediately after this, the mixture was cooled rapidly to 0° C., and a 2 μl aliquot was subjected to an electrophoresis on a 6% denature polyacrylamide gel using a HITACHI 5500-S DNA sequencer system. The results are shown in FIG. 1.

Example 3

Polyacrylamide Gel Electrophoresis Analysis

To 10 μl in total of 5 mM sodium phosphate buffer (pH7.0), a standard reaction solution containing 10 nM of the DNA fragment (pUC-I') whose 5'-terminal had been labeled with the texas red, 10% (v/v) DMF and an agent at the concentration indicated in FIG. 2 was added in a microcentrifugation tube (Eppendorf) and allowed to stand for 5 minutes, 1 hour and 2 hours, respectively at 23° C.

[Lanes 1, DNA control, Lanes 2-4, 100, 50, 25 nM (13), Lanes 5-7, 100, 50, 25 nM (13); Lanes 8-10, 100, 50, 25 nM (13); Lanes 11-13, 100, 50, 25 nM (1)]

After each reaction time, a bovine thymus DNA (1 mM, 1 μL) was added for quenching, and the mixture was shaken for 5 minutes at 90° C. The DNA obtained by centrifugation under reduced pressure was combined with 8 μl of a loading color (solution of *FUGENE* Red in DMF) and dissolved, and then shaken for 20 minutes at 94° C. Immediately after this, the mixture was cooled rapidly to 0° C., and a 2 μl aliquot was subjected to an electrophoresis on a 6% denature polyacrylamide gel using a HITACHI 5500-S DNA sequencer system. The results are shown in FIG. 2.

Example 4

Analysis of Alkylation Reaction on DNA Oligomer

A DNA oligomer synthesized by a DNA synthesizer was employed. To 50 μl in total of 50 mM sodium cacodylate buffer (pH7.0), a standard reaction solution containing 150 μM of the double-stranded DNA fragment, 10% (v/v) DMF and each agent of Compounds 1, 12, 13 and 14 (150 μM) was added in a microcentrifugation tube (Eppendorf) and allowed to stand at 23° C.

The advancement of the reaction was ensured by an HPLC using a *CHEMCOBOND* 5-ODS-H column (4.6×150 mm). The HPLC conditions are shown below.

[Linear gradient of 50 mM ammonium formate: 0-50% acetonitrile (0 to 40 min), flow rate: 1.0 mL/min, 254 nm].

The results are shown in FIG. 3.

Example 5

Polyacrylamide Gel Electrophoresis Analysis

To 10 μl in total of 5 mM sodium phosphate buffer (pH7.0), a standard reaction solution containing 10 nM of the DNA fragment (pUC-II) whose 5'-terminal had been labeled with the texas red, 10% (v/v) DMF and an agent at the concentration indicated in FIG. 4 was added in a microcentrifugation tube (Eppendorf) and allowed to stand for 24 hours at 23° C.

[Lane 1, DNA control; Lanes 2-7, 50, 25, 12.5, 10, 7.5, 5, 2.5 nM (15); Lanes 8-13, 50, 25, 12.5, 10, 7.5, 5, 2.5 nM (16); Lanes 14-19, 50, 25, 12.5, 10, 7.5, 5, 2.5 nM (14)]

A bovine thymus DNA (1 mM, 1 μL) was added for quenching, and the mixture was shaken for 5 minutes at 90° C. The DNA obtained by centrifugation under reduced pressure was combined with 8 μl of a loading color (solution of *FUGENE* Red in DMF) and dissolved, and then shaken for 20 minutes at 94° C. Immediately after this, the mixture was cooled rapidly to 0° C., and 2 μl aliquot was subjected to an electrophoresis on a 6% denature polyacrylamide gel using a HITACHI 5500-S DNA sequencer system. The results are shown in FIG. 4.

Example 6

Polyacrylamide Gel Electrophoresis Analysis

To 10 μl in total of 5 mM sodium phosphate buffer (pH7.0), a standard reaction solution containing 10 nM of the DNA fragment (pUC-II) whose 5'-terminal had been labeled with the texas red, 10% (v/v) DMF and an agent at the concentration indicated in FIG. 5 was added in a microcentrifugation tube (Eppendorf) and allowed to stand for 24 hours at 23° C.

[Lanes 1-5, 50, 25, 12.5, 6.3 nM (16); Lanes 6-10, 50, 25, 12.5, 6.3 nM (23)]

A bovine thymus DNA (1 mM, 1 μL) was added for quenching, and the mixture was shaken for 5 minutes at 90° C. The DNA obtained by centrifugation under reduced pressure was combined with 8 μl of a loading color (solution of *FUGENE* Red in DMF) and dissolved, and then shaken for 20 minutes at 94° C. Immediately after this, the mixture was cooled rapidly to 0° C., and 2 μl aliquot was subjected to an electrophoresis on a 6% denature polyacrylamide gel using a HITACHI 5500-S DNA sequencer system. The results are shown in FIG. 5.

Examples 7 to 9

Synthesis of Compounds 12, 13 and 14

According to the reaction scheme 1, Compounds 12, 13 and 14 were synthesized.

(1) Synthesis of AcImPyPy-γ-$CO_2CH_3$ (4)

To a solution of Compound 2 (1.0 g, 3.72 mmol) in a mixture of methanol and ethyl acetate (1:1, 30 mL), 10% palladium-carbon (220 mg) was added and the mixture was stirred for 3 hours at room temperature under a hydrogen atmosphere. The catalyst was filtered off through Celite, and the filtrate was concentrated to obtain a crude amine (859 mg), which was used in the next reaction without further purification. The crude amine (859 mg, 3.59 mmol) was dissolved in 15 ml of DMF, to which Compound 3 (820 mg, 2.69 mmol) and FDPP: pentafluorophenyldiphenyl phosphinate (1.70 g, 4.42 mmol) were added and then $^iPr_2NEt$: diisopropylethylamine (1.54 mL, 8.84 mmol) was added. The reaction mixture was stirred for 24 hours at room temperature, and the solvent in the reaction solution was distilled off to obtain a residue, which was purified by a column chromatography on a silica gel (eluted with the gradient of 0 to 10% MeOH/$CHCl_3$) to obtain Compound 4 (1.33 g) at the yield of 94%.

$^1$H NMR (DMSO-$d_6$) δ 10.23 (s, 1H), 9.94 (s, 1H), 9.88 (s, 1H), 8.02 (brt, 1H), 7.42 (s, 1H), 7.27 (d, J=1.5 Hz, 1H), 7.17 (d, J=1.5 Hz, 1H), 7.12 (d, J=1.5 Hz, 1H), 6.87 (d, J=1.5 Hz, 1H), 3.95 (s, 3H), 3.85 (s, 3H), 3.80 (s, 3H), 3.59 (s, 3H), 3.16 (dt, J=6.0, 7.0 Hz, 2H), 2.34 (t, J=7.0 Hz, 2H), 2.03 (s, 3H), 1.74 (qu, J=7.0 Hz, 2H).

ESMS m/e calcd for $C_{24}$; $H_{31}$; $N_{,8}$; $O_{,6}$ (M+H) 527.2. found 527.1.

(2) Synthesis of AcImPyPy-γ-$CO_2H$ (5)

Compound 4 (1.33 g, 2.52 mmol) was suspended in 50 ml of distilled water, and combined with sodium hydroxide (800 mg, 20 mmol). The mixture was stirred for 24 hours at room temperature, treated with a 10% aqueous solution of HCl at 0° C. to make acidic (pH2). The precipitate formed was recovered by filtration, washed with water, dried to obtain Compound 5 (1.10 g) at the yield of 85%.

$^1$H NMR (DMSO-$d_6$) δ 10.24 (s, 1H), 9.95 (s, 1H), 9.89 (s, 1H), 8.02 (brt, 1H), 7.42 (s, 1H), 7.26 (d, J=1.5 Hz, 1H), 7.17 (d, J=1.5 Hz, 1H), 7.11 (d, J=1.5 Hz, 1H), 6.86 (d, J=1.5 Hz, 1H), 3.94 (s, 3H), 3.84 (s, 3H), 3.78 (s, 3H), 3.17 (dt, J=6.0, 7.0 Hz, 2H), 2.24 (t, J=7.0 Hz, 2H), 2.01 (s, 3H), 1.79 (qu, J=7.0 Hz, 2H).

ESMS m/e calcd for $C_{23}$; $H_{29}$; $N_{,8}$; $O_{,6}$ (M+H) 513.2. found 513.3.

(3) Synthesis of $NO_2$ImPyPyL$CO_2CH_2CH_3$ (8c)

To a solution of Compound 6 (500 mg, 2.23 mmol) in a mixture of methanol and ethyl acetate (1:1, 20 mL), a 10% palladium-carbon (200 mg) was added. After adding a suspension of sodium borohydride (170 mg, 4.47 mmol) suspended in distilled water (1 ml) dropwise at 0° C., the reaction mixture was stirred for 20 minutes at room temperature under a nitrogen atmosphere. The catalyst was filtered off through a silica gel, and the filtrate was concentrated to obtain a crude amine (418 mg), which was used in the next reaction without further purification. The crude amine (418 mg, 2.15 mmol) was dissolved in 14 ml of DMF, to which Compound 7 (330 mg, 1.13 mmol) and FDPP: pentafluorophenyldiphenyl phosphinate (1.3 g, 3.39 mmol) were added and then $^i$Pr$_2$NEt: diisopropylethylamine (1.18 mL, 6.78 mmol) was added. The reaction mixture was stirred for 20 hours, and the solvent in the reaction solution was distilled off to obtain a residue, which was purified by a column chromatography on a silica gel (eluted with the gradient of 0 to 10% MeOH/CHCl$_3$) to obtain Compound 8c (359 mg) at the yield of 83%.

$^1$H NMR (DMSO-d$_6$) δ 10.86 (s, 1H), 9.98 (s, 1H), 8.61 (s, 1H), 7.51 (d, J=16.0 Hz, 1H), 7.41 (s, 1H), 7.30 (s, 1H), 7.22 (s, 1H), 6.74 (s, 1H), 6.07 (d, J=16.0 Hz, 1H), 4.14 (q, J=7.0 Hz, 2H), 4.05 (s,3H), 3.85 (s, 3H), 3.68 (s, 3H), 1.23 (t, J=7.0 Hz, 3H).

ESMS m/e calcd for C$_{,21}$; H$_{,24}$; N$_{,7}$; O$_{,6}$ (M+H) 470.2. found 470.1.

(4) Synthesis of AcImPyPy-γ-ImPyPyCO$_2$CH$_3$ (9a)

To a solution of Compound 8a (200 mg, 0.466 mmol) in a mixture of methanol and ethyl acetate (1:1, 8 mL), a 10% palladium-carbon (100 mg) was added and the mixture was stirred for 5 hours at room temperature under a hydrogen atmosphere. The catalyst was filtered off through Celite, and the filtrate was concentrated to obtain a crude amine (178 mg), which was used in the next reaction without further purification. The crude amine (178 mg, 0.446 mmol) was dissolved in 2 ml of DMF, to which Compound 5 (190 mg, 0.373 mmol) and FDPP: pentafluorophenyldiphenyl phosphinate (268 mg, 0.699 mmol) were added and then $^i$Pr$_2$NEt: diisopropylethylamine (0.243 mL, 1.39 mmol) was added. The reaction mixture was stirred for 16 hours at room temperature, and the solvent in the reaction solution was distilled off to obtain a residue, which was purified by a column chromatography on a silica gel (eluted with the gradient of 0 to 10% MeOH/CHCl$_3$) to obtain Compound 9a (154.5 mg) at the yield of 49%.

$^1$H NMR (DMSO-d$_6$) δ 10.26 (s, 1H), 10.23 (s, 1H), 9.99 (s, 1H), 9.96 (s, 1H), 9.94 (s, 1H), 9.90 (s, 1H), 8.02 (brt, 1H), 7.45 (s, 1H), 7.42 (s, 2H), 7.26 (s, 2H), 7.17 (s, 1H), 7.14 (s, 1H), 7.12 (s, 1H), 6.89 (s, 1H), 6.88 (s, 1H), 3.94 (s, 6H), 3.84 (s, 3H), 3.83 (s, 3H), 3.82 (s, 3H), 3.81 (s, 3H), 3.79 (s, 3H), 3.20 (m, 2H), 2.35 (m, 2H), 2.01 (s, 3H), 1.78 (m, 2H).

ESMS m/e calcd for C$_{,41}$; H$_{,48}$; N$_{,15}$; O$_{,9}$ (M+H) 894.4. found 894.3.

(5) Synthesis of AcImPyPy-γ-ImPyLCO$_2$CH$_2$CH$_3$ (9b)

To a solution of Compound 8b (68 mg, 0.20 mmol) in a mixture of methanol and ethyl acetate (1:1, 4 mL), a 10% palladium-carbon (30 mg) was added. After adding a suspension of sodium borohydride (20 mg, 0.528 mmol) suspended in distilled water (0.2 ml) dropwise at 0° C., the reaction mixture was stirred for 20 minutes at room temperature under a nitrogen atmosphere. The catalyst was filtered off through a silica gel, and the filtrate was concentrated to obtain a crude amine (60 mg), which was used in the next reaction without further purification. The crude amine (60 mg, 0.189 mmol) was dissolved in 0.6 ml of DMF, to which Compound 5 (97 mg, 0.189 mmol) and FDPP: pentafluorophenyldiphenyl phosphinate (109 mg, 0.284 mmol) were added and then $^i$Pr$_2$NEt: diisopropylethylamine (99 µl, 0.568 mmol) was added. The reaction mixture was stirred for 18 hours and the solvent in the reaction solution was distilled off to obtain a residue, which was purified by a column chromatography on a silica gel (eluted with the gradient of 0 to 10% MeOH/CHCl$_3$) to obtain Compound 9b (107 mg) at the yield of 69%.

$^1$H NMR (DMSO-d$_6$) δ 10.27 (s, 1H), 10.23 (s, 1H), 9.95 (s,1H), 9.89 (s, 2H), 8.01 (brt, 1H), 7.51 (d, J=16.0 Hz, 1H), 7.45 (s, 1H), 7.43 (d, J=1.0 Hz, 1H), 7.42 (s, 1H), 7.27 (d, J=1.0 Hz, 1H), 7.17(d, J=2.0 Hz, 1H), 7.12 (d, J=2.0 Hz, 1H), 6.89 (d, J=2.0 Hz, 1H), 6.83 (d, J=2.0 Hz, 1H), 6.11 (d, J=16.0 Hz, 1H), 4.15 (q, J=7.0 Hz, 2H), 3.95 (s, 3H), 3.94 (s, 3H), 3.85 (s, 3H), 3.80 (s, 3H), 3.69 (s, 3H), 3.20 (dt, J=5.5, 7.0 Hz, 2H), 2.36 (t, J=7.0 Hz, 2H), 2.02 (s, 3H), 1.79(q, J=7.0 Hz, 2H), 1.24 (t, J=7.0 Hz, 3H).

ESMS m/e calcd for C$_{,38}$; H$_{,46}$; N$_{,13}$; O$_{,8}$ (M+H) 812.4. found 812.3.

Compounds 7 and 8 used as starting materials in the section (3) described above, Compound 8a used as a starting material in the section (4) described above and Compound 8b used as a starting material in the section (5) described above were synthesized in accordance with the description in J. Am. Chem. Soc. 1999, 121, 4961 and J. Am. Chem. Soc. 2000, 122, 1602 and the like.

(6) Synthesis of AcImPyPy-γ-ImPyPyLCO$_2$CH$_2$CH$_3$ (9c)

Compound 9c was obtained by the synthetic procedure similar to that for Compound 9b at the yield of 28%.

$^1$H NMR (DMSO-d$_6$) δ 10.26 (s, 1H), 10.23 (s, 1H), 9.97 (s,1H), 9.95 (s, 1H), 9.94 (s, 1H), 9.89 (s, 1H), 8.02 (brt, 1H), 7.52 (d, J=16.0 Hz, 1H), 7.46 (s, 1H), 7.42 (s, 1H), 7.41 (s, 1H), 7.27 (s, 2H), 7.17 (s, 1H), 7.15 (s, 1H), 7.13 (s, 1H), 6.90 (s, 1H), 6.75 (s, 1H), 6.08 (d, J=16.0 Hz, 1H), 4.15 (q, J=7.0 Hz, 2H), 3.95 (s, 3H), 3.94 (s, 3H), 3.85 (s, 3H), 3.84 (s, 3H), 3.80 (s, 3H), 3.69 (s, 3H), 3.21 (m, 2H), 2.36 (m, 2H), 2.02 (s, 3H), 1.79 (m, 2H), 1.24 (t, J=7.0 Hz, 3H).

ESMS m/e calcd for C$_{,44}$; H$_{,52}$; N$_{,15}$; O$_{,9}$ (M+H) 934.4. found 934.4.

(7) Synthesis of AcImPyPy-γ-ImPyPyCO$_2$H (10a)

To a suspension of Compound 9a (154.5 mg, 0.181 mmol) in 0.6 ml of distilled water, 1,8-diazabicyclo[5.4.0]-7-undecene (DBU) (0.2 ml, 1.34 mmol) was added. This reaction mixture was stirred for 2 hours, treated with 1% aqueous solution of HCl at 0° C. to make acidic (pH2). The precipitate formed was recovered by filtration, washed with water, dried to obtain Compound 10a (131.5 mg) at the yield of 86%.

$^1$H NMR (DMSO-d$_6$) δ 10.25 (s, 1H), 10.23 (s, 1H), 9.97 (s, 1H), 9.95 (s, 1H), 9.90 (s, 1H), 9.89 (s, 1H), 8.02 (brt, 1H), 7.45 (s, 1H), 7.41 (s, 2H), 7.26 (s, 2H), 7.17 (s, 1H), 7.12 (s, 2H), 6.89 (s, 1H), 6.84 (s, 1H), 3.94 (s, 6H), 3.84 (s, 3H), 3.83 (s, 3H), 3.81 (s, 3H), 3.79 (s, 3H), 3.18 (m, 2H), 2.35 (m, 2H), 2.01 (s, 3H), 1.78 (m, 2H).

ESMS m/e calcd for C$_{,40}$; H$_{,46}$; N$_{,15}$; O$_{,9}$ (M+H) 880.4. found 880.4.

(8) Synthesis of AcImPyPy-γ-ImPyLCO$_2$H (10b)

To a suspension of Compound 9b (143 mg, 0.176 mmol) in 0.6 ml of distilled water, DBU (0.6 ml, 4.01 mmol) was added. This reaction mixture was stirred for 6 hours, and then the solvent was distilled off to obtain a residue, which was washed with diethyl ether and ethyl acetate. After purification by a column chromatography on a silica gel (eluted with the gradient of 0 to 20% MeOH/CHCl$_3$), a crude crystalline carboxylate was made acidic with 1% acetic acid. The precipitate formed was recovered by filtration, washed with water and dried to obtain Compound 10b (70 mg) at the yield of 51%.

$^1$H NMR (DMSO-$d_6$) δ 10.27 (s, 1H), 10.23 (s, 1H), 9.95 (s, 1H), 9.89 (s, 2H), 8.02 (brt, 1H), 7.46 (d, J=16.0 Hz, 1H), 7.45 (s, 1H), 7.42 (s, 1H), 7.41 (s, 1H), 7.27 (d, J=2.0 Hz, 1H), 7.17 (s, 1H), 7.13 (d, J=2.0 Hz, 1H), 6.89 (d, J=2.0 Hz, 1H), 6.80 (d, J=2.0 Hz, 1H), 6.03 (d, J=16.0 Hz, 1H), 3.95 (s, 3H), 3.94 (s, 3H), 3.85 (s, 3H), 3.80(s, 3H), 3.68 (s, 3H), 3.21 (m, 2H), 2.36 (m, 2H), 2.03 (s, 3H), 1.79 (m,2H).

ESMS m/e calcd for $C_{36}$; $H_{42}$; $N_{13}$; $O_8$ (M+H) 784.3. found 784.3.

(9) Synthesis of AcImPyPy-γ-ImPyPyLCO$_2$H (10c)

Compound 10c was obtained at the yield of 50% by the synthetic procedure similar to that for Compound 10b using Compound 9c instead of Compound 9b.

$^1$H NMR (DMSO-$d_6$) δ 10.24 (s, 1H), 10.21 (s, 1H), 9.95 (s, 1H), 9.93 (s, 1H), 9.91 (s, 1H), 9.88 (s, 1H), 8.01 (brt, 1H), 7.45 (d, J=16.0 Hz, 1H), 7.44 (s, 1H), 7.41 (s, 1H), 7.37 (s, 1H), 7.26 (s, 2H), 7.16 (s, 1H), 7.12 (s, 1H), 7.11 (s, 1H), 6.88 (s, 1H), 6.70 (s, 1H), 5.99 (d, J=16.0 Hz, 1H), 3.94 (s, 6H), 3.84 (s, 6H), 3.79 (s, 3H), 3.66 (s, 3H), 3.20 (m, 2H), 2.35 (m, 2H), 2.01 (s, 3H), 1.78 (m, 2H).

ESMS m/e calcd for $C_{42}$; $H_{48}$; $N_{15}$; $O_9$ (M+H) 906.4. found 906.3.

(10) Synthesis of AcImPyPy-γ-ImPyPyLCOIm (11a)

Compound 10a (10 mg, 11.3 µmol) was dissolved in DMF (0.2 ml) and combined with 1,1'-carbonyldiimidazole (3.5 mg, 22.0 µmol). This reaction mixture was stirred for 5 hours at room temperature. The solvent was distilled off under reduced pressure to obtain a yellow residue, which was washed three times with diethyl ether (5 ml) to obtain Compound 11a (10 mg) at the yield of 95%.

$^1$H NMR (DMSO-$d_6$) δ 10.25 (s, 1H), 10.23 (s, 1H), 10.06 (s,1H), 10.03 (s, 1H), 9.96 (s, 1H), 9.90 (s, 1H), 8.26 (s, 1H), 8.01 (brt,1H), 7.77 (s, 1H), 7.69 (s, 1H), 7.45 (s, 1H), 7.41 (s, 1H), 7.26 (s, 2H), 7.20 (s, 1H), 7.17 (s, 1H), 7.13 (s, 2H), 6.95 (s, 1H), 6.89 (s, 1H), 3.94 (s, 6H), 3.90 (s, 3H), 3.85 (s, 3H), 3.84 (s, 3H), 3.79 (s, 3H), 3.20 (m, 2H), 2.35 (m, 2H), 2.01 (s, 3H), 1.78 (m, 2H).

ESMS m/e calcd for $C_{43}$; $H_{48}$; $N_{17}$; $O_8$ (M+H) 930.4. found 930.3.

(11) Synthesis of AcImPyPy-γ-ImPyLCOIm (11b)

Compound 11b was obtained at the yield of 94% by the synthetic procedure similar to that for Compound 11a using Compound 10b instead of Compound 10a.

$^1$H NMR (DMSO-$d_6$) δ 10.26 (s, 1H), 10.23 (s, 1H), 10.08 (s,1H), 9.95 (s, 1H), 9.89 (s, 1H), 8.68 (s, 1H), 8.02 (brt, 1H), 7.90 (s, 1H), 7.87 (d, J=15.0 Hz, 1H), 7.63 (s, 1H), 7.49 (s, 1H), 7.47 (s, 1H), 7.42 (s, 1H), 7.31 (s, 1H), 7.27 (s, 1H), 7.18 (s, 1H), 7.14 (d, J=15.0 Hz, 1H), 7.13 (s, 1H), 6.90 (s, 1H), 3.96 (s, 3H), 3.95 (s, 3H), 3.86 (s,3H), 3.81 (s, 3H), 3.78 (s, 3H), 3.21 (m, 2H), 2.37 (m, 2H), 2.02 (s, 3H), 1.80 (m, 2H).

ESMS m/e calcd for $C_{39}$; $H_{44}$; $N_{15}$; $O_7$ (M+H) 834.4. found 834.3.

(12) Synthesis of AcImPyPy-γ-ImPyPyLCOIm (11c)

Compound 11c was obtained at the yield of 94% by the synthetic procedure similar to that for Compound 11a using Compound 10c instead of Compound 10a.

$^1$H NMR (DMSO-$d_6$) δ 10.24 (s, 1H), 10.21 (s, 1H), 10.04 (s, 1H), 9.99 (s, 1H), 9.94 (s, 1H), 9.88 (s, 1H), 8.66 (s, 1H), 8.01 (brt, 1H), 7.89 (s, 1H), 7.87 (d, J=15.0 Hz, 1H), 7.63 (s, 1H), 7.47 (s, 1H), 7.45 (s, 1H), 7.41 (s, 1H), 7.28 (s, 1H), 7.25 (s, 1H), 7.22 (s, 1H), 7.16 (s, 1H), 7.13 (d, J=15.0 Hz, 1H), 7.11 (s, 1H), 7.09 (s, 1H), 6.89 (s, 1H), 3.95 (s, 3H), 3.94 (s, 3H), 3.86 (s, 3H), 3.84 (s, 3H), 3.79 (s,3H), 3.77 (s, 3H), 3.20 (m, 2H), 2.35 (m, 2H), 2.01 (s, 3H), 1.79 (m, 2H).

ESMS m/e calcd for $C_{45}$; $H_{50}$; $N_{17}$; $O_8$ (M+H) 956.4. found 956.5.

(13) Synthesis of AcImPyPy-γ-ImPyPyCPI (12)

To an anhydrous DMF (0.1 ml) solution of sodium hydride (3.0 mg, 75 µmol, 60% suspension in mineral oil), an anhydrous DMF (0.1 ml) solution of the segment A of the DU86 (3.7 mg, 14.5 µmol) was added and then an anhydrous DMF (0.1 ml) solution of Compound 11a (10 mg, 10.7 µmol) was added at 0° C., and the reaction mixture was stirred for 1 hour at 0° C. The reaction was quenched by adding 50 mM sodium phosphate buffer (2 mL, pH6.86) at 0° C., and the solvent was distilled off under reduced pressure to obtain a yellow residue. This crude crystal was purified by a column chromatography on a silica gel (eluted with the gradient of 0 to 5% MeOH/CHCl$_3$) to obtain Compound 12 (5.7 mg) at the yield of 49%. After a further purification by an HPLC using a *CHEMCOBOND* 5-ODS-H column (eluted with a linear gradient of 0.1% AcOH/CH$_3$CN 0-50%, 35.1 min/40 min, 254 nm), the resultant Compound 12 was used in the DNA alkylation reaction described above.

$^1$H NMR (DMSO-$d_6$) δ 12.37 (brs, 1H), 10.25 (s, 1H), 10.22 (s,1H), 9.96 (s, 1H), 9.94 (s, 1H), 9.93 (s, 1H), 9.88 (s, 1H), 8.01 (brt, 1H), 7.44 (s, 2H), 7.41 (s, 1H), 7.25 (s, 2H), 7.16 (s, 1H), 7.14 (s, 1H), 7.12 (s, 1H), 6.88 (s, 1H), 6.70 (s, 1H), 6.14 (s, 1H), 4.22 (m, 1H), 4.08 (m, 1H), 3.94 (s, 6H), 3.84 (s, 6H), 3.79 (s, 3H), 3.73 (s, 3H), 3.72 (s, 3H), 3.42 (m, 1H), 3.21 (m, 2H), 2.41 (s, 3H), 2.34 (m, 2H), 2.17(m, 1H), 2.01 (s, 3H), 1.78 (m, 2H), 1.41 (m, 1H).

ESMS m/e calcd for $C_{54}$; $H_{58}$; $N_{17}$; $O_{11}$ (M+H) 1120.4. found 1120.5.

(14) Synthesis of AcImPyPy-γ-ImPyLCPI (13)

Compound 13 was obtained at the yield of 50% by the synthetic procedure similar to that for Compound 12 using Compound 11b instead of Compound 11a. After a further purification by an HPLC using a *CHEMCOBOND* 5-ODS-H column (eluted with a linear gradient of 0.1% AcOH/CH$_3$CN 0-50%, 32.9 min/40 min, 254 nm), the resultant Compound 13 was used in the DNA alkylation reaction described above.

$^1$H NMR (DMSO-$d_6$) δ 12.18 (brs, 1H), 10.26 (s, 1H), 10.22 (s, 1H), 10.19 (s, 1H), 9.94 (s, 1H), 9.89 (s, 1H), 8.02 (brt, 1H), 7.57(d, J=15.0 Hz, 1H), 7.46 (s, 1H), 7.42 (s, 1H), 7.34 (s, 1H), 7.27 (s, 1H), 7.18 (s, 1H), 7.13 (s, 1H), 6.98 (s, 1H), 6.89 (s, 1H), 6.58 (d, J=15.0 Hz, 1H), 5.96 (s, 1H), 4.28 (m, 1H), 4.15 (m, 1H), 3.95 (s, 6H), 3.85 (s, 3H), 3.80 (s, 3H), 3.73 (s, 3H), 3.72 (s, 3H), 3.54 (m, 1H), 3.20(m, 2H), 2.46 (s, 3H), 2.36 (m, 2H), 2.09 (m, 1H), 2.02 (s, 3H), 1.79 (m, 2H), 1.29 (m, 1H).

ESMS m/e calcd for $C_{50}$; $H_{54}$; $N_{15}$; $O_{10}$ (M+H) 1024.4. found 1024.4.

(15) Synthesis of AcImPyPy-γ-ImPyPyLCPI (14)

Compound 14 was obtained at the yield of 51% by the synthetic procedure similar to that for Compound 12 using Compound 11c instead of Compound 11a. After a further purification by an HPLC using a *CHEMCOBOND* 5-ODS-H column (eluted with a linear gradient of 0.1%

AcOH/CH₃CN 0-50%, 36.8 min/40 min, 254 nm), the resultant Compound 14 was used in the DNA alkylation reaction described above.

¹H NMR (DMSO-d₆) δ 12.37 (brs, 1H), 10.26 (s, 1H), 10.22 (s,1H), 10.19 (s, 1H), 9.97 (s, 1H), 9.94 (s, 1H), 9.89 (s, 1H), 8.02 (brt,1H), 7.58 (d, J=15.0 Hz, 1H), 7.46 (s, 1H), 7.42 (s, 1H), 7.39 (s, 1H), 7.28 (s, 1H), 7.27 (s, 1H), 7.17 (s, 1H), 7.15 (s, 1H), 7.13 (s, 1H), 6.90 (s, 2H), 6.58 (d, J=15.0 Hz, 1H), 6.00 (s, 1H), 4.29 (m, 1H), 4.15 (m, 1H), 3.96 (s, 3H), 3.95 (s, 3H), 3.86 (s, 3H), 3.85 (s, 3H), 3.80 (s,3H), 3.73 (s, 3H), 3.72 (s, 3H), 3.54 (m, 1H), 3.19 (m, 2H), 2.47 (s, 3H), 2.38 (m, 2H), 2.09 (m, 1H), 2.02 (s, 3H), 1.80 (m, 2H), 1.29 (m, 1H).

ESMS m/e calcd for $C_{56}$; $H_{60}$; $N_{17}$; $O_{11}$ (M+H) 1146.5. found 1146.5.

Examples 10 and 11

Synthesis of Compounds 15 and 16

Compounds 15 and 16 were synthesized as shown in the scheme 2 in accordance with the synthetic procedure for Compounds 13 and 14 shown in the reaction scheme 1.

(1) AcImPyPy-γ-ImPyPyLCPI (15):
¹H NMR (DMSO-d₆) δ 10.30 (s, 1H), 10.27 (s, 2H), 10.24 (s, 1H), 9.94 (s, 1H), 9.90 (s, 2H), 9.31 (brs, 1H), 8.00 (brt, 1H), 7.57 (d, J=14.5 Hz, 1H), 7.56 (s, 1H), 7.50 (s, 1H), 7.45 (s, 1H), 7.37 (s, 1H), 7.27 (s, 2H), 7.17 (s, 1H), 7.15 (s, 2H), 6.89 (s, 2H), 6.55 (d, J=14.5 Hz, 1H), 6.48 (s, 1H), 4.26 (m, 1H), 4.18 (m, 1H), 4.00 (s, 3H), 3.97 (s,3H), 3.95 (s, 3H), 3.85 (s, 3H), 3.80 (s, 6H), 3.72 (s, 3H), 3.71 (s, 3H), 3.50 (m, 1H), 3.16 (m, 2H), 2.47 (s, 3H), 2.35 (m, 2H), 2.15 (m, 1H), 2.03 (s, 3H), 1.79 (m, 2H), 1.30 (m, 1H).

ESMS m/e calcd for $C_{61}$; $H_{65}$; $N_{20}$; $O_{12}$ (M+H) 1269.5. found 1269.4.

(2) H-ImImPyPy-γ-ImPyPyLCPI (16):
¹H NMR (DMSO-d₆) δ 12.34 (brs, 1H), 10.30 (s, 2H), 10.23 (s,1H), 9.94 (s, 1H), 9.87 (s, 1H), 9.68 (s, 1H), 8.00 (brt, 1H), 7.57 (d, J=14.5 Hz, 1H), 7.55 (s, 2H), 7.45 (s, 1H), 7.44 (s, 2H), 7.37 (s, 1H), 7.27 (s, 2H), 7.17 (s, 1H), 7.14 (s, 2H), 7.06 (s, 1H), 6.89 (s, 1H), 6.55 (d, J=14.5 Hz, 1H), 4.27 (m, 1H), 4.13 (m, 1H), 4.00 (s, 6H), 3.95 (s, 3H), 3.85 (s, 3H), 3.84 (s, 3H), 3.80 (s, 3H), 3.72 (s, 3H), 3.71 (s,3H), 3.45 (m, 1H), 3.15 (m, 2H), 2.47 (s, 3H), 2.35 (m, 2H), 2.17 (m, 1H), 1.78 (m, 2H), 1.30 (m, 1H).

ESMS m/e calcd for $C_{59}$; $H_{62}$; $N_{19}$; $O_{11}$ (M+H) 1212.5. found 1212.5.

Example 12

Synthesis of Compound 23

Compound 23 was synthesized in accordance with the synthetic procedure for Compounds 13 to 16 shown in the reaction schemes 1 and 2 except for using 1,2,9,9a-tetrahydrocyclopropa[c]benz[e]indole-4-one instead of the segment A (Du86) of the DU-86 in the final step.

H-ImImPyPy-γ-ImPyPyLCBI (23):
¹H NMR (DMSO-d₆) δ 10.30 (s, 1H), 10.23 (s, 1H), 9.96 (s, 1H), 9.95 (s, 1H), 9.90 (s, 1H), 9.68 (s, 1H), 7.99 (brt, 1H), 7.98 (d, J=8.0 Hz, 1H), 7.61-6.89 (m, 17H), 6.57 (d, J=15.0 Hz, 1H), 4.33 (m, 1H), 4.28 (m, 1H), 4.00 (s, 6H), 3.94 (s, 3H), 3.85 (s, 3H), 3.84 (s, 3H), 3.80(s, 3H), 3.72 (s, 3H), 3.68 (m, 1H), 3.18 (m, 2H), 2.35 (m, 2H), 1.79 (m,2H), 1.70 (m, 1H), 1.55 (m, 1H).

ESMS m/e calcd for $C_{58}$; $H_{59}$; $N_{18}$; $O_{9}$ (M+H) 1151.5. found 1151.5.

INDUSTRIAL APPLICABILITY

The invention relates to a design of a functional molecule having high DNA-alkylating ability and sequence-recognizing ability on a specific base sequence existing on a DNA. The base sequence-recognizing ability of such a functional molecule can be altered by changing the position of the imidazole-pyrrole in the molecule. The only alkylating agent having such a property is the alkylating agent developed by the inventors. This fact allows a gene-level drug development leading the post-genome period to be realized for the first time whereby providing a drug useful against a significant gene sequence in a human genome as well as against a gene aberration derived from a disease such as a cancer.

The invention claimed is:

1. A hairpin polyamide having an alkylation reaction site via a vinyl linker on the terminal of a pyrrole-imidazole polyamide, wherein the hairpin polyamide is a compound represented by Formula [2]:

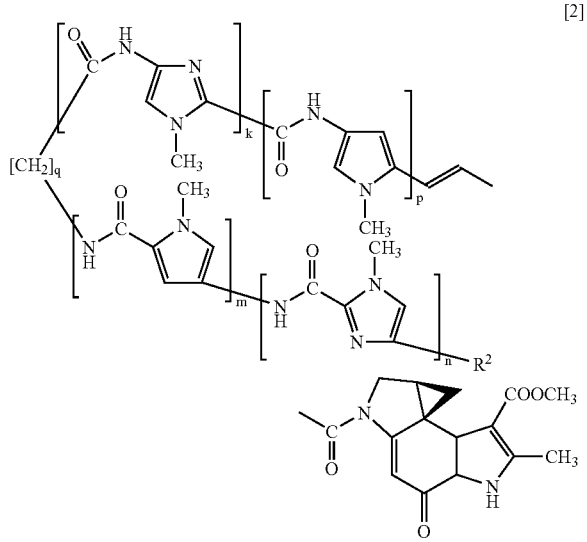

[2]

in which $R^2$ is a hydrogen, an alkyl group or an acetamide group, and k, p, q, m and n represents a natural number from 1 to 10 respectively or Formula [3]:

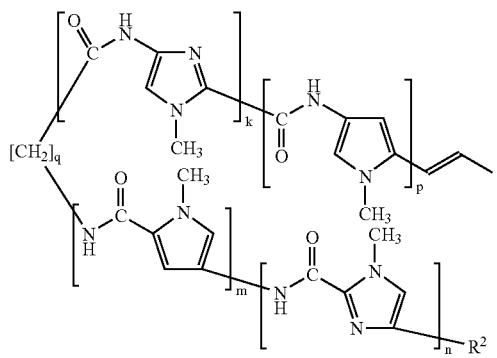

[3]

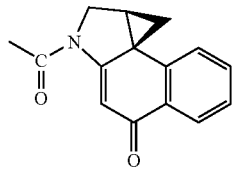

in which $R^2$ is a hydrogen, an alkyl group or an acetamide group, and k, p, q, m and n represents a natural number from 1 to 10 respectively.

2. The hairpin polyamide according to claim 1 wherein the compound represented by Formula [2] is a compound represented by the following structural formula:

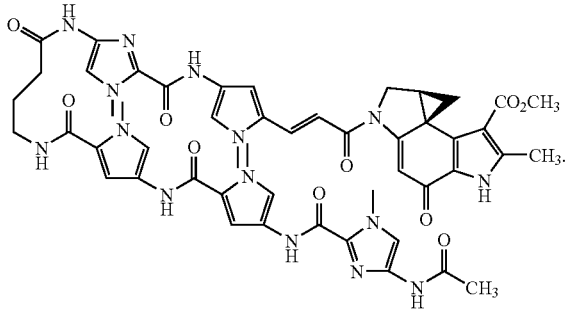

3. The hairpin polyamide according to claim 1 wherein the compound represented by Formula [2] is a compound represented by the following structural formula:

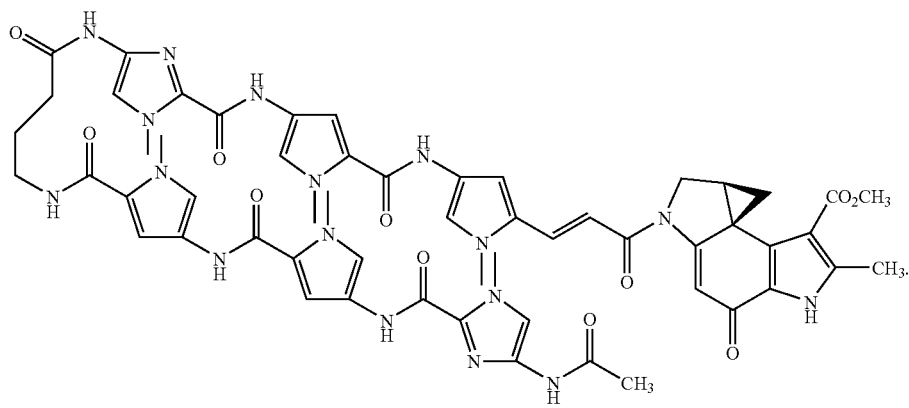
4. The hairpin polyamide according to claim 1 wherein the compound represented by Formula [2] is a compound represented by the following structural formula:
5. The hairpin polyamide according to claim 1 wherein the compound represented by Formula [2] is a compound represented by the following structural formula:
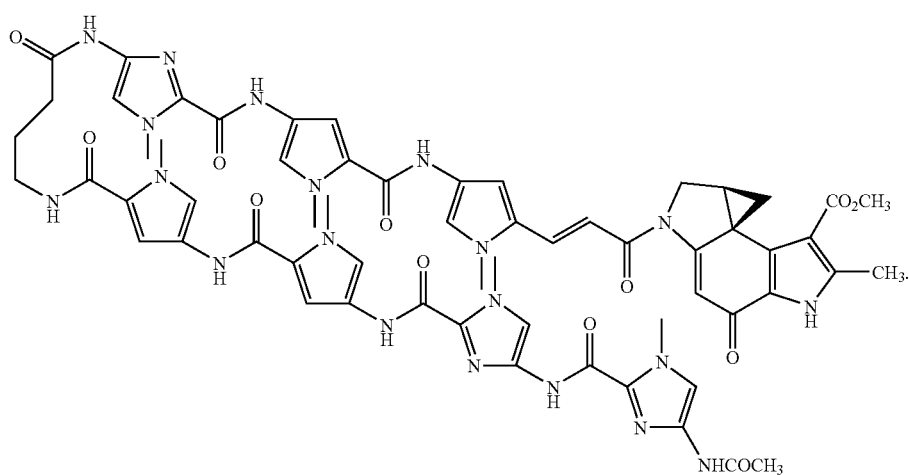

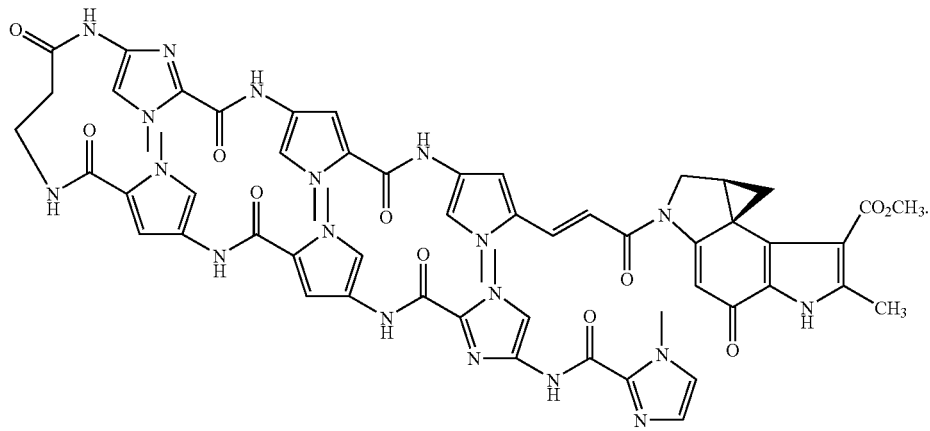
6. The hairpin polyamide according to claim 1 wherein the compound represented by Formula [3] is a compound represented by the following structural formula:
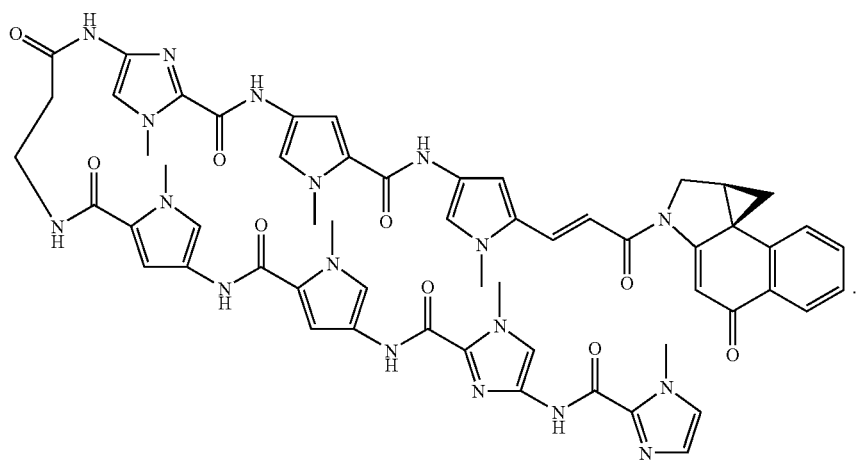
7. An agent for inhibiting the expression of a specific gene which comprises a hairpin polyamide according to any of claims 1, 2-5 and 6.
8. An agent according to claim 7 wherein said specific gene is an abnormal gene.
* * * * *

SEQUENCE LISTING

```
<160> NUMBER OF SEQ ID NOS: 22

<210> SEQ ID NO 1
<211> LENGTH: 10
<212> TYPE: DNA
<213> ORGANISM: Artificial
<220> FEATURE:
<223> OTHER INFORMATION: DNA Oligomer

<400> SEQUENCE: 1
caagtcagag                                                          10

<210> SEQ ID NO 2
<211> LENGTH: 10
<212> TYPE: DNA
<213> ORGANISM: Artificial
<220> FEATURE:
<223> OTHER INFORMATION: DNA Oligomer

<400> SEQUENCE: 2
```

```
ctctgacttg                                                           10

<210> SEQ ID NO 3
<211> LENGTH: 20
<212> TYPE: DNA
<213> ORGANISM: Artificial
<220> FEATURE:
<223> OTHER INFORMATION: DNA Primer

<400> SEQUENCE: 3
agaatcaggg gataacgcag                                                20

<210> SEQ ID NO 4
<211> LENGTH: 20
<212> TYPE: DNA
<213> ORGANISM: Artificial
<220> FEATURE:
<223> OTHER INFORMATION: DNA Primer

<400> SEQUENCE: 4
ttaccagtgg ctgctgccag                                                20

<210> SEQ ID NO 5
<211> LENGTH: 21
<212> TYPE: DNA
<213> ORGANISM: Artificial
<220> FEATURE:
<223> OTHER INFORMATION: DNA Primer

<400> SEQUENCE: 5
tgctggcctt ttgctcacat g                                              21

<210> SEQ ID NO 6
<211> LENGTH: 18
<212> TYPE: DNA
<213> ORGANISM: Artificial
<220> FEATURE:
<223> OTHER INFORMATION: DNA Primer

<400> SEQUENCE: 6
tgtaaaacga cggccagt                                                  18

<210> SEQ ID NO 7
<211> LENGTH: 40
<212> TYPE: DNA
<213> ORGANISM: Artificial
<220> FEATURE:
<223> OTHER INFORMATION: DNA Oligomer

<400> SEQUENCE: 7
ccggtaacta tcgtcttgag tccaacccgg taagacacga                          40

<210> SEQ ID NO 8
<211> LENGTH: 40
<212> TYPE: DNA
<213> ORGANISM: Artificial
<220> FEATURE:
<223> OTHER INFORMATION: DNA Oligomer

<400> SEQUENCE: 8
ggccattgat agcagaactc aggttgggcc attctgtgct                          40

<210> SEQ ID NO 9
<211> LENGTH: 32
<212> TYPE: DNA
<213> ORGANISM: Artificial
```

```
<220> FEATURE:
<223> OTHER INFORMATION: DNA Oligomer

<400> SEQUENCE: 9
caagtcagag gtggcgaaac ccgacaggac ta                          32

<210> SEQ ID NO 10
<211> LENGTH: 32
<212> TYPE: DNA
<213> ORGANISM: Artificial
<220> FEATURE:
<223> OTHER INFORMATION: DNA Oligomer

<400> SEQUENCE: 10
gttcagtctc caccgctttg ggctgtcctg at                          32

<210> SEQ ID NO 11
<211> LENGTH: 28
<212> TYPE: DNA
<213> ORGANISM: Artificial
<220> FEATURE:
<223> OTHER INFORMATION: DNA Oligomer

<400> SEQUENCE: 11
cctgacgagc atcacaaaaa tcgacgct                               28

<210> SEQ ID NO 12
<211> LENGTH: 28
<212> TYPE: DNA
<213> ORGANISM: Artificial
<220> FEATURE:
<223> OTHER INFORMATION: DNA Oligomer

<400> SEQUENCE: 12
ggactgctcg tagtgttttt agctgcga                               28

<210> SEQ ID NO 13
<211> LENGTH: 11
<212> TYPE: DNA
<213> ORGANISM: Artificial
<220> FEATURE:
<223> OTHER INFORMATION: DNA Oligomer

<400> SEQUENCE: 13
gtaagacacg a                                                 11

<210> SEQ ID NO 14
<211> LENGTH: 11
<212> TYPE: DNA
<213> ORGANISM: Artificial
<220> FEATURE:
<223> OTHER INFORMATION: DNA Oligomer

<400> SEQUENCE: 14
cattctgtgc t                                                 11

<210> SEQ ID NO 15
<211> LENGTH: 38
<212> TYPE: DNA
<213> ORGANISM: Artificial
<220> FEATURE:
<223> OTHER INFORMATION: DNA Oligomer

<400> SEQUENCE: 15
cctgacgagc atcacaaaaa tcgacgctca agtcagag                    38
```

```
<210> SEQ ID NO 16
<211> LENGTH: 38
<212> TYPE: DNA
<213> ORGANISM: Artificial
<220> FEATURE:
<223> OTHER INFORMATION: DNA Oligomer

<400> SEQUENCE: 16
ggactgctcg tagtgttttt agctgcgagt tcagtctc                              38

<210> SEQ ID NO 17
<211> LENGTH: 10
<212> TYPE: DNA
<213> ORGANISM: Artificial
<220> FEATURE:
<223> OTHER INFORMATION: DNA Oligomer

<400> SEQUENCE: 17
caagtcagag                                                             10

<210> SEQ ID NO 18
<211> LENGTH: 10
<212> TYPE: DNA
<213> ORGANISM: Artificial
<220> FEATURE:
<223> OTHER INFORMATION: DNA Oligomer

<400> SEQUENCE: 18
gttcagtctc                                                             10

<210> SEQ ID NO 19
<211> LENGTH: 16
<212> TYPE: DNA
<213> ORGANISM: Artificial
<220> FEATURE:
<223> OTHER INFORMATION: DNA Oligomer

<400> SEQUENCE: 19
agctatgacc atgatt                                                      16

<210> SEQ ID NO 20
<211> LENGTH: 16
<212> TYPE: DNA
<213> ORGANISM: Artificial
<220> FEATURE:
<223> OTHER INFORMATION: DNA Oligomer

<400> SEQUENCE: 20
tcgatactgg tactaa                                                      16

<210> SEQ ID NO 21
<211> LENGTH: 10
<212> TYPE: DNA
<213> ORGANISM: Artificial
<220> FEATURE:
<223> OTHER INFORMATION: DNA Oligomer

<400> SEQUENCE: 21
cttgacttca                                                             10
```

```
<210> SEQ ID NO 22
<211> LENGTH: 10
<212> TYPE: DNA
<213> ORGANISM: Artificial
<220> FEATURE:
<223> OTHER INFORMATION: DNA Oligomer

<400> SEQUENCE: 22
gaactgaagt                                                          10
```